(12) United States Patent
Uchida et al.

(10) Patent No.: US 10,642,005 B2
(45) Date of Patent: May 5, 2020

(54) IMAGE PICKUP APPARATUS AND OPTICAL APPARATUS USING THE SAME

(71) Applicant: OLYMPUS CORPORATION, Hachioji-shi, Tokyo (JP)

(72) Inventors: Yoshihiro Uchida, Hachioji (JP); Keisuke Takada, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 233 days.

(21) Appl. No.: 15/946,296

(22) Filed: Apr. 5, 2018

(65) Prior Publication Data

US 2018/0224636 A1    Aug. 9, 2018

Related U.S. Application Data

(63) Continuation of application No. PCT/JP2015/078894, filed on Oct. 13, 2015.

(51) Int. Cl.
| | | |
|---|---|---|
| G02B 13/04 | (2006.01) | |
| A61B 1/00 | (2006.01) | |
| A61B 1/04 | (2006.01) | |
| G02B 9/34 | (2006.01) | |
| G02B 13/00 | (2006.01) | |
| G02B 13/18 | (2006.01) | |
| B60R 11/04 | (2006.01) | |
| B60R 11/00 | (2006.01) | |

(52) U.S. Cl.
CPC .......... *G02B 13/04* (2013.01); *A61B 1/00096* (2013.01); *A61B 1/041* (2013.01); *G02B 9/34* (2013.01); *G02B 13/004* (2013.01); *G02B 13/18* (2013.01); *B60R 11/04* (2013.01); *B60R 2011/004* (2013.01)

(58) Field of Classification Search
CPC .................................................. H01L 21/67248
USPC .......................................................... 359/753
See application file for complete search history.

(56) References Cited

U.S. PATENT DOCUMENTS

| 7,471,465 B2 | 12/2008 | Yamashita et al. |
|---|---|---|
| 2009/0278920 A1 | 11/2009 | Kamo |
| 2013/0120859 A1* | 5/2013 | Tsai .................... G02B 13/0035 359/716 |

FOREIGN PATENT DOCUMENTS

| JP | 10020189 A | 1/1998 |
|---|---|---|
| JP | 2008281859 A | 11/2008 |

(Continued)

OTHER PUBLICATIONS

Japanese Office Action dated Aug. 19, 2019 issued in counterpart Japanese Application No. 2017-545017.

(Continued)

*Primary Examiner* — James C. Jones
(74) *Attorney, Agent, or Firm* — Holtz, Holtz & Volek PC

(57) ABSTRACT

An image pickup apparatus includes an optical system which includes a plurality of lenses and an aperture stop, and an image sensor which is disposed at an image position of the optical system, wherein the optical system includes in order from an object side, a first lens having a negative refractive power, a second lens having a negative refractive power, a third lens having a positive refractive power, and a fourth lens, and the following conditional expressions (1) and (3) are satisfied:

αmax−αmin<4.0×10⁻⁵/° C.    (1), and 0.2<D1Ls/DsF<3.0    (3).

23 Claims, 18 Drawing Sheets

(56) References Cited

FOREIGN PATENT DOCUMENTS

| JP | 2009276371 | A | 11/2009 |
| JP | 4613111 | B2 | 1/2011 |
| JP | 4744184 | B2 | 8/2011 |
| JP | 2014232283 | A | 12/2014 |
| JP | 2015011050 | A | 1/2015 |

OTHER PUBLICATIONS

International Preliminary Report on Patentability (IPRP) (and English language translation thereof) dated Apr. 26, 2018 issued in counterpart International Application No. PCT/JP2015/078894.
International Search Report (ISR) dated Dec. 8, 2015 issued in International Application No. PCT/JP2015/078894.
Written Opinion dated Dec. 8, 2015 issued in International Application No. PCT/JP2015/078894.

* cited by examiner

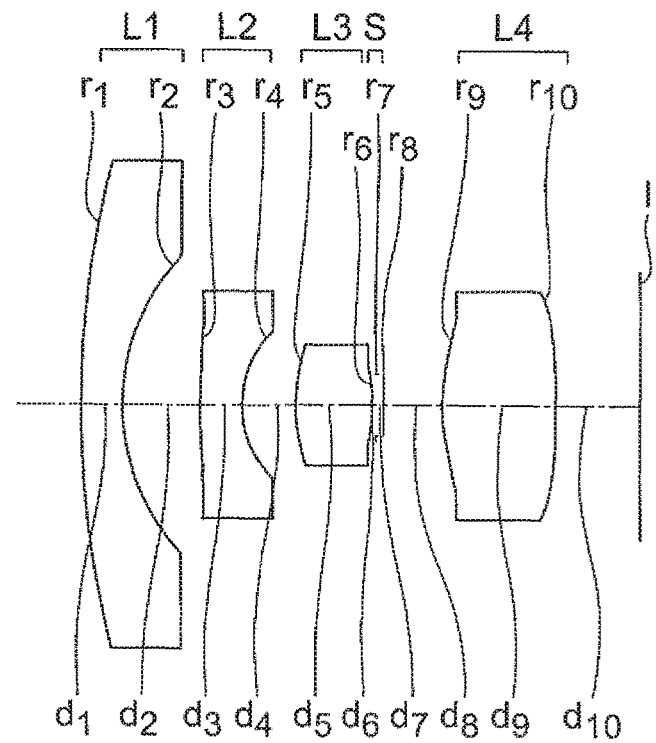
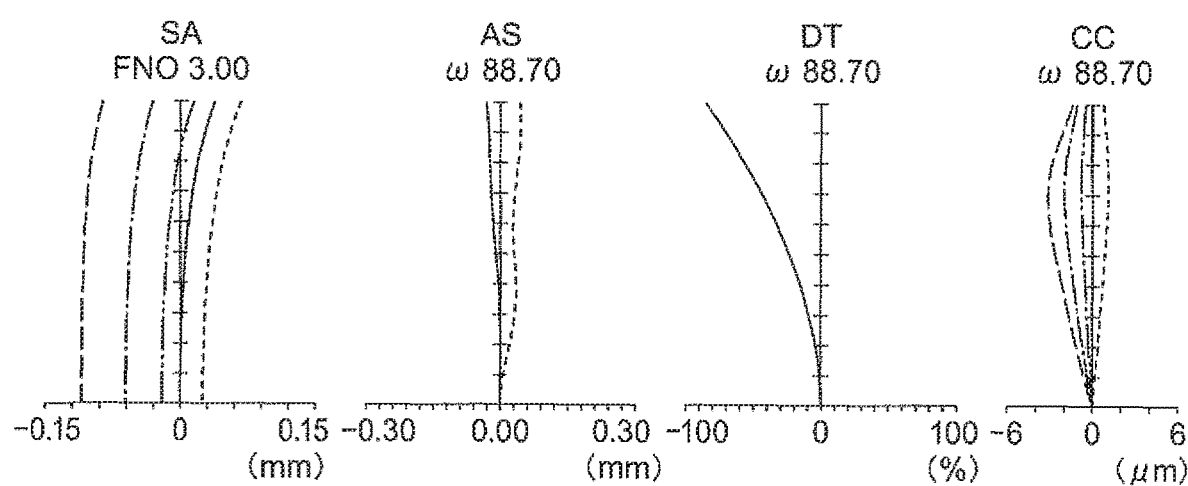

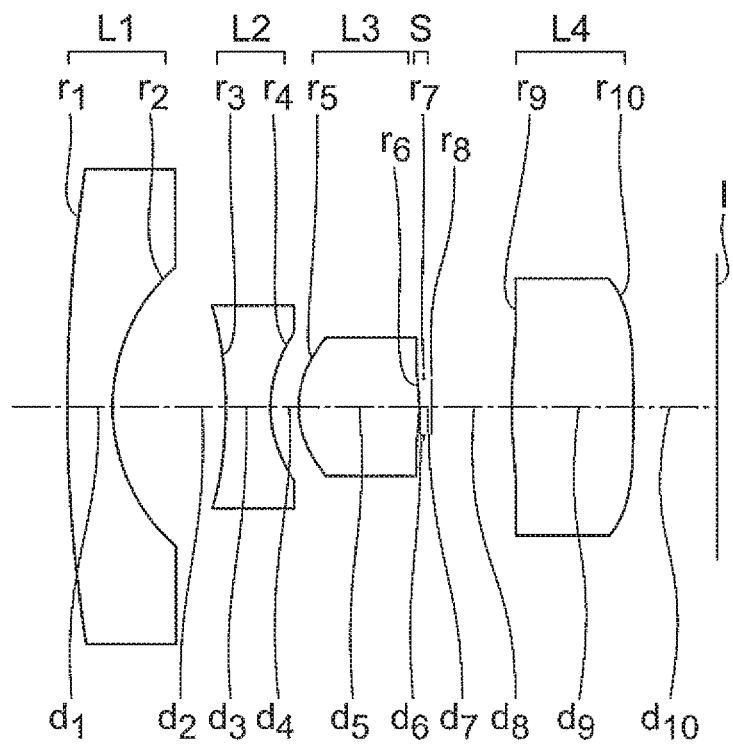
FIG. 4A
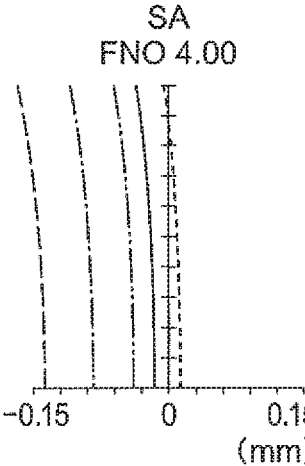
FIG. 4B
SA
FNO 4.00
FIG. 4C
AS
ω 85.35
FIG. 4D
DT
ω 85.35
FIG. 4E
CC
ω 85.35

SA
FNO 4.50

AS
ω 87.20

DT
ω 87.20

CC
ω 87.20

SA
FNO 4.50
-0.15  0  0.15
(mm)

AS
ω 82.70
-0.30  0.00  0.30
(mm)

DT
ω 82.70
-100  0  100
(%)

CC
ω 82.70
-6  0  6
(μm)

SA
FNO 2.80

AS
ω 82.75

DT
ω 82.75

CC
ω 82.75

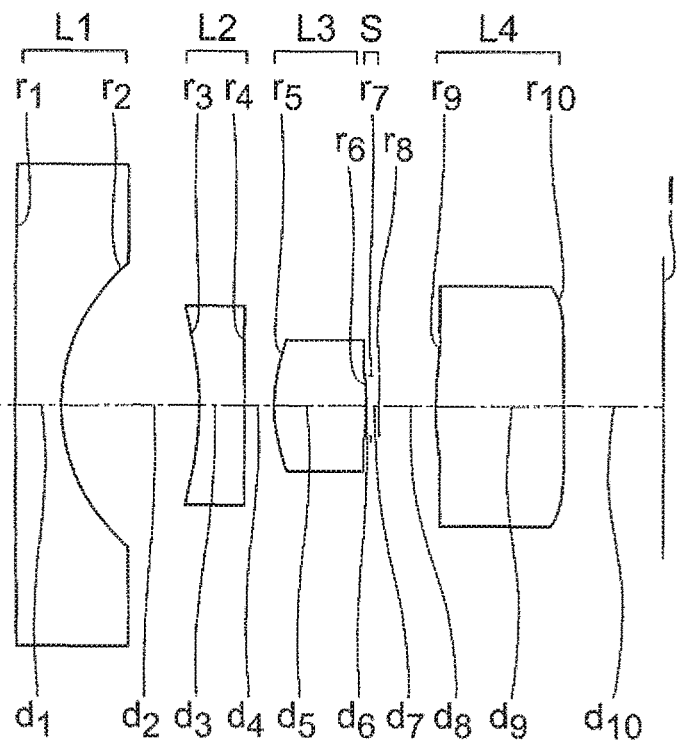
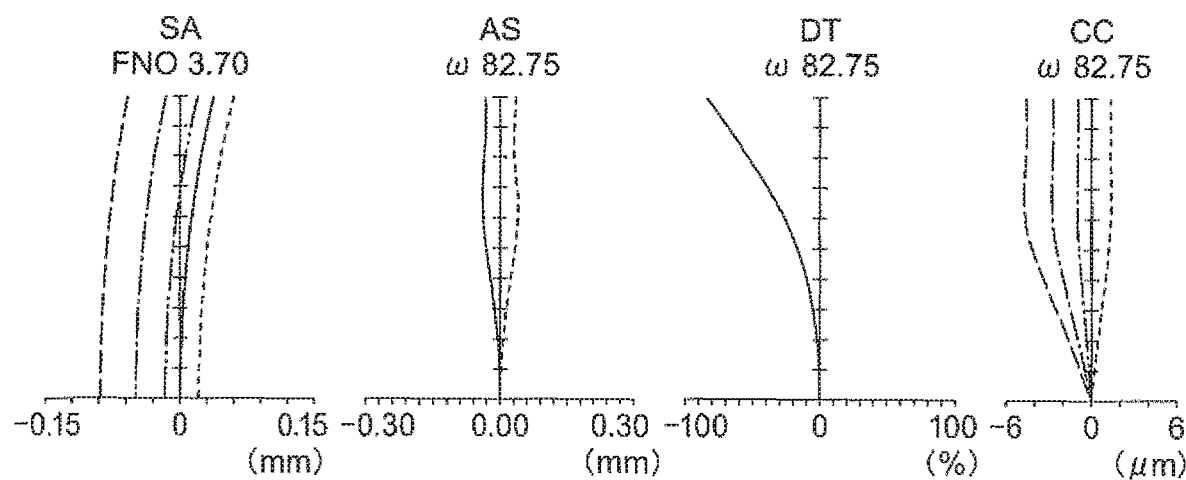

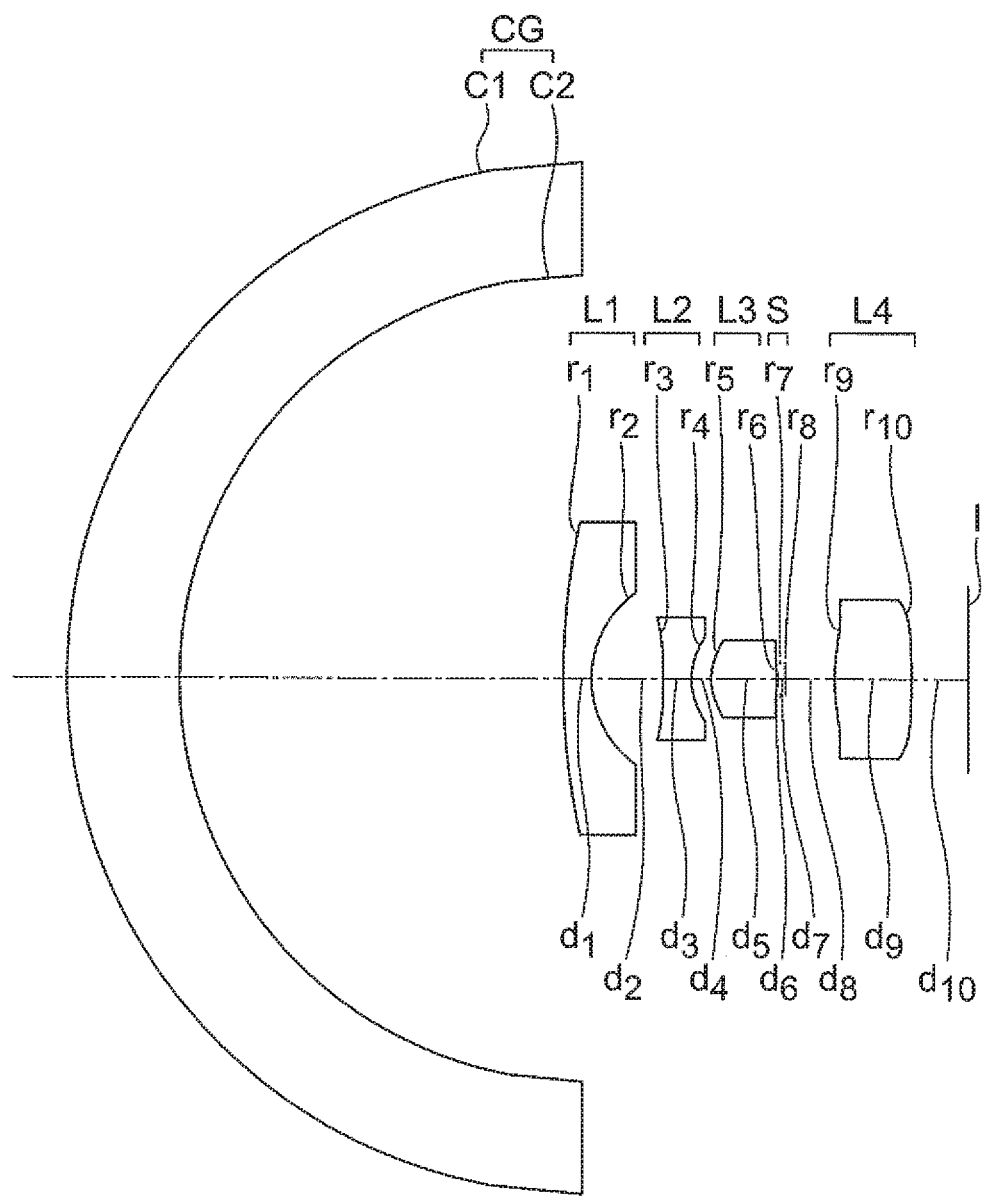

IMAGE PICKUP APPARATUS AND OPTICAL APPARATUS USING THE SAME

CROSS-REFERENCE TO RELATED APPLICATION

The present application is a continuation application of International Application No. PCT/JP2015/078894 filed on Oct. 13, 2015, the entire contents of which are incorporated herein by reference.

BACKGROUND OF THE INVENTION

Field of the Invention

The present invention relates to an image pickup apparatus and an optical apparatus using the same.

Description of the Related Art

For capturing a wide range, an image pickup apparatus which includes an objective optical system having a wide angle of view, and an image sensor has been proposed. A CCD (charge coupled device) or CMOS (complementary metal-oxide semiconductor) etc. are used in the image sensor. In recent years, small-sizing and making the number of pixels large, have been progressing in image sensors. With this, a small-sizing of an objective optical system to be used in an image pickup apparatus has been sought.

Furthermore, light-weighting has been sought in an image pickup apparatus that is to be mounted in an optical apparatus such as an endoscope having a scope unit (hereinafter, referred to as 'scope type endoscope'), a capsule endoscope, and a mobile telephone. For this, an objective optical system in which a resin has been used for a material of a lens has been proposed. Moreover, an objective optical system which includes a small number of lenses has been proposed.

In Japanese Patent No. 4744184 Publication, a super-wide angle lens which includes four lenses has been disclosed. The super-wide angle lens includes a first lens having a negative refractive power, a second lens having a negative refractive power, a third lens having a positive refractive power, an aperture stop, and a fourth lens having a positive refractive power. Moreover, a resin has been used for a material of at least one lens.

In Japanese Patent No. 4613111 Publication, an optical system which includes three to five lenses has been disclosed. This optical system includes a lens unit having a negative refractive power, a meniscus lens in which an object-side is convex, an aperture stop, and a biconvex positive lens. Moreover, a resin has been used for a material of at least one lens.

SUMMARY OF THE INVENTION

An image pickup apparatus according to the present invention comprises:
an optical system which includes a plurality of lenses and an aperture stop, and
an image sensor which is disposed at an image position of the optical system, wherein
the optical system includes in order from an object side,
a first lens having a negative refractive power,
a second lens having a negative refractive power,
a third lens having a positive refractive power, and
a fourth lens, and the following conditional expressions (1) and (3) are satisfied:

$$\alpha max - \alpha min < 4.0 \times 10^{-5}/°C. \quad (1), \text{ and}$$

$$0.2 < D1Ls/DsF < 3.0 \quad (3),$$

where, $\alpha$ max denotes a largest coefficient of linear expansion among coefficients of linear expansion at 20 degrees of the plurality of lenses, $\alpha$ min denotes a smallest coefficient of linear expansion among the coefficients of linear expansion at 20 degrees of the plurality of lenses, D1Ls denotes a distance on an optical axis from an object-side surface of the first lens up to an object-side surface of the aperture stop, and DsF denotes a distance on the optical axis from an image-side surface of the aperture stop up to a lens surface positioned nearest to image.

Moreover, an optical apparatus of the present invention comprises;
an image pickup apparatus, and
a signal processing circuit.

BRIEF DESCRIPTION OF THE DRAWINGS

FIG. 2A, and FIG. 2B, FIG. 2C, FIG. 2D, and FIG. 2E are a cross-sectional view and aberration diagrams of an optical system of an example 2;

FIG. 4A, and FIG. 4B, FIG. 4C, FIG. 4D, and FIG. 4E are a cross-sectional view and aberration diagrams of an optical system of an example 4;

FIG. 10A, and FIG. 10B, FIG. 10C, FIG. 10D, and FIG. 10E are a cross-sectional view and aberration diagrams of an optical system of an example 10;

FIG. 16 is a cross-sectional view of an optical system of an example 16;

DETAILED DESCRIPTION OF THE INVENTION

Figure 1A:
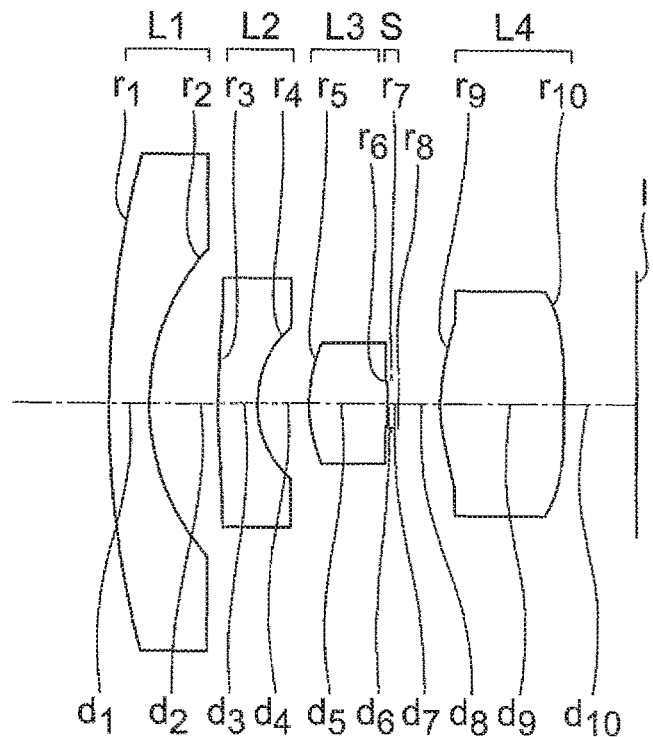
FIG. 1A, and FIG. 1B, FIG. 1C, FIG. 1D, and FIG. 1E are a cross-sectional view and aberration diagrams of an optical system of an example 1.
Figure 1B:
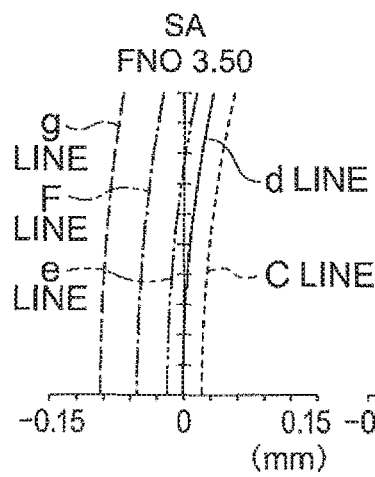
Figures 1C, 1D:
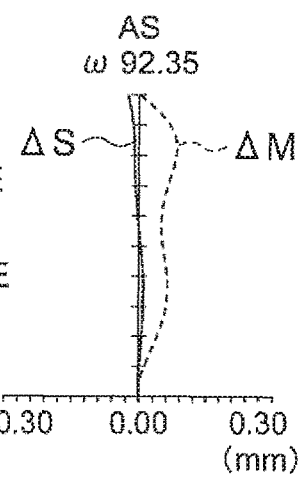
Figure 1E:
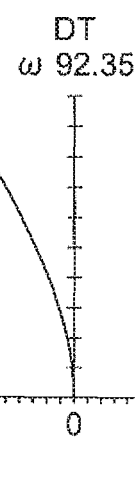
Figure 3A:
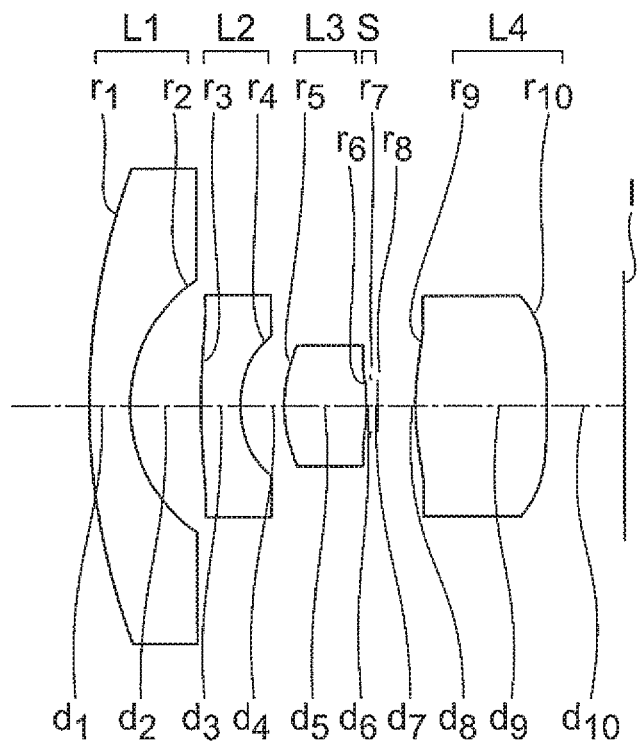
FIG. 3A, and FIG. 3B, FIG. 3C, FIG. 3D, and FIG. 3E are a cross-sectional view and aberration diagrams of an optical system of an example 3.
Figures 3B, 3C, 3D, 3E:
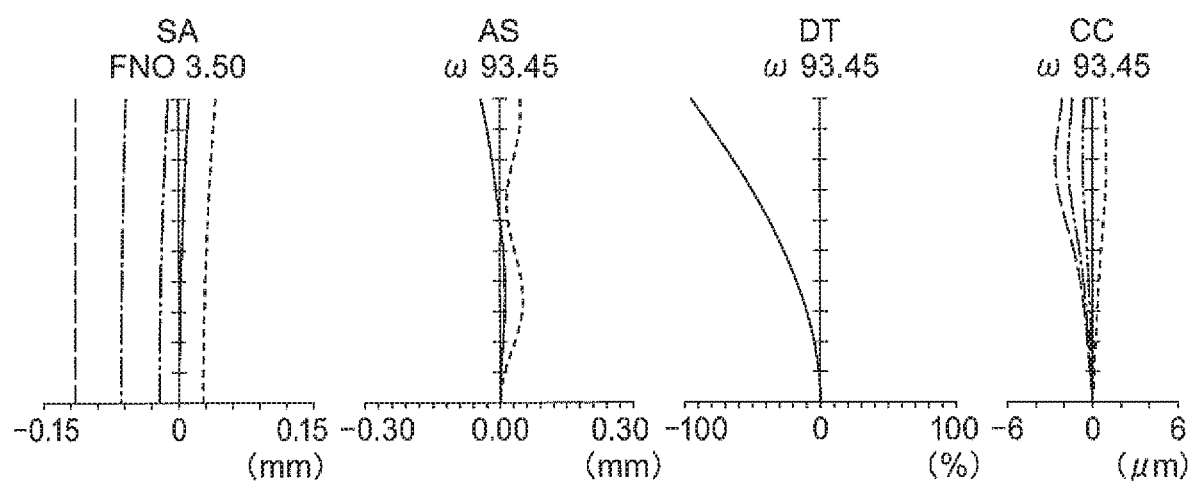
Figure 5A:
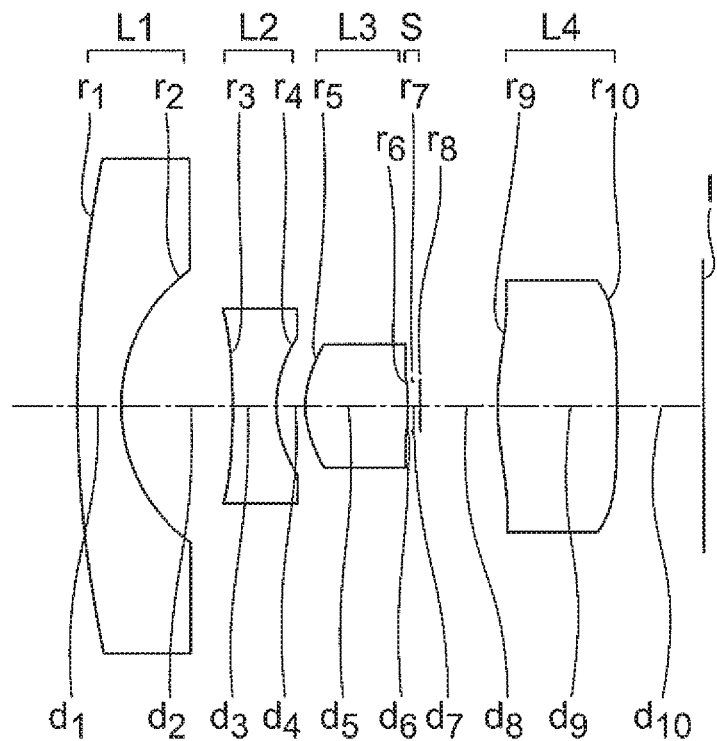
FIG. 5A, and FIG. 5B, FIG. 5C, FIG. 5D, and FIG. 5E are a cross-sectional view and aberration diagrams of an optical system of an example 5.
Figure 5B:
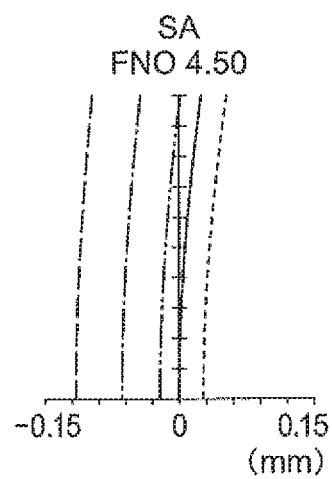
Figure 5C:
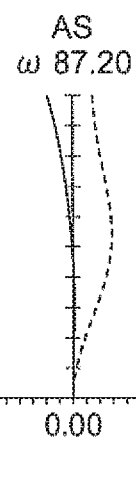
Figure 5D:
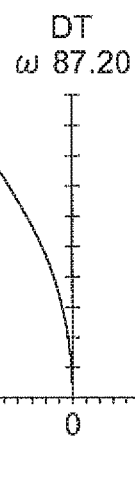
Figure 5E:
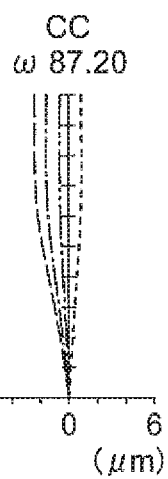
Figure 6A:
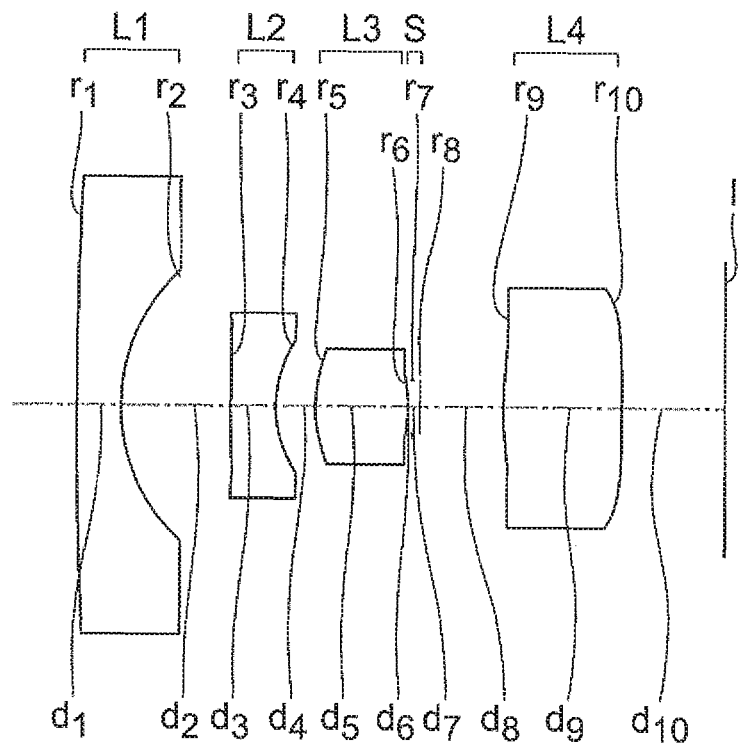
FIG. 6A, and FIG. 6B, FIG. 6C, FIG. 6D, and FIG. 6E are a cross-sectional view and aberration diagrams of an optical system of an example 6.
Figure 6B:
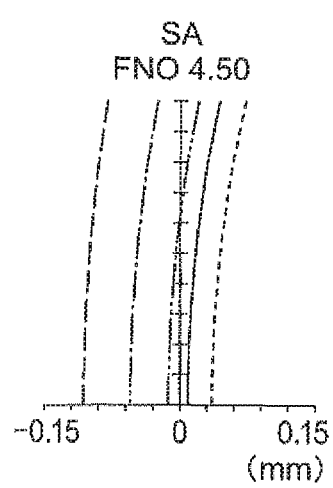
Figure 6C:
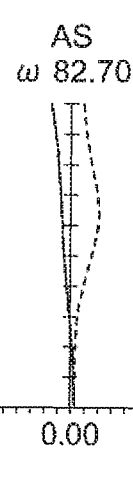
Figure 6D:
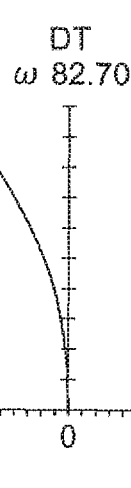
Figure 6E:
Figure 7A:
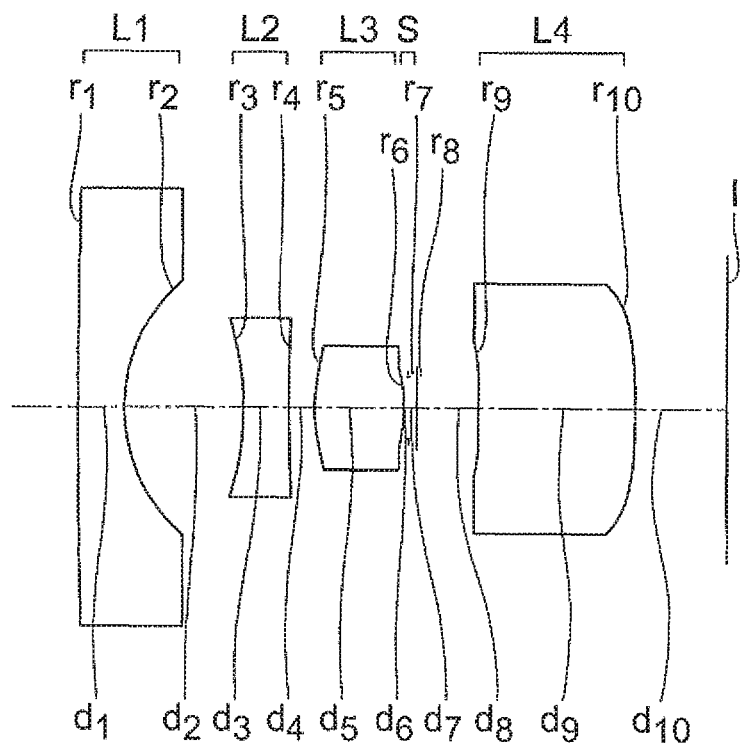
FIG. 7A, and FIG. 7B, FIG. 7C, FIG. 7D, and FIG. 7E are a cross-sectional view and aberration diagrams of an optical system of an example 7.
Figures 7B, 7C, 7D, 7E:
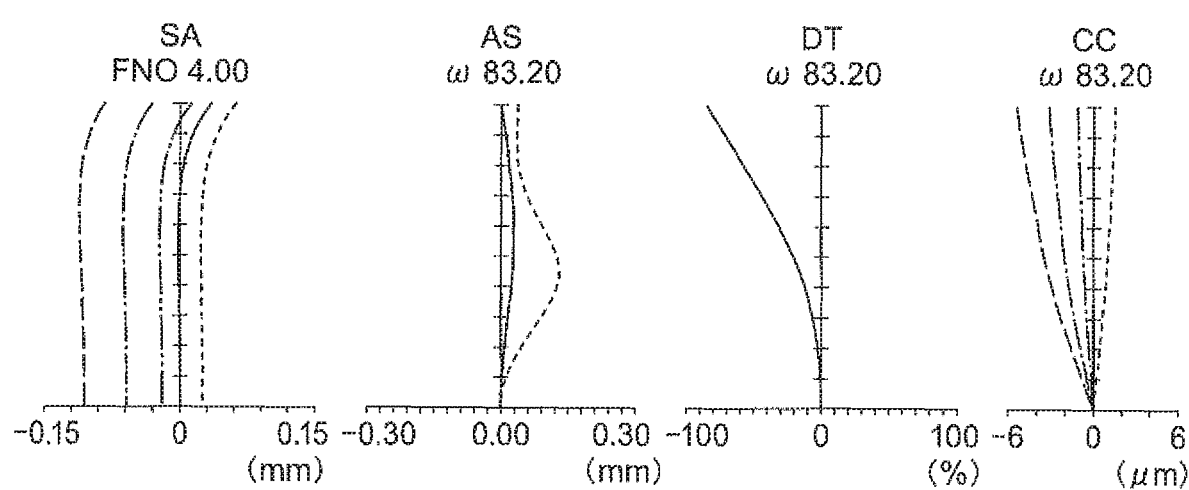
Figure 8A:
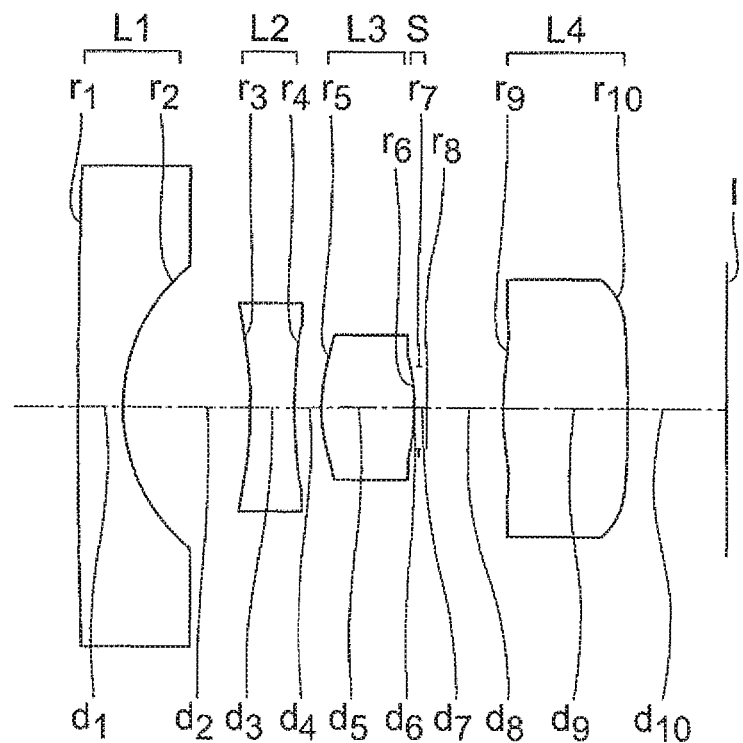
FIG. 8A, and FIG. 8B, FIG. 8C, FIG. 8D, and FIG. 8E are a cross-sectional view and aberration diagrams of an optical system of an example 8.
Figure 8B:
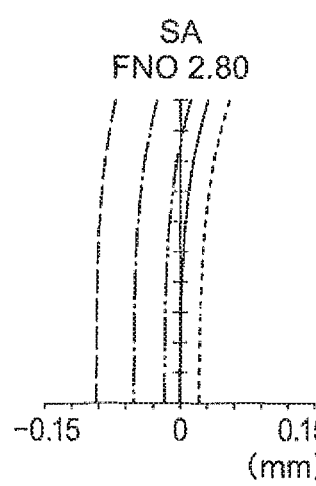
Figure 8C:
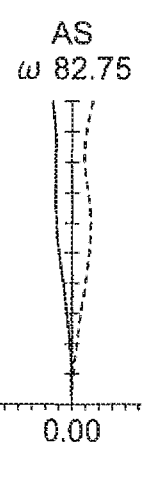
Figure 8D:
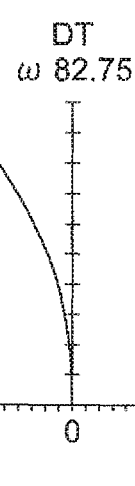
Figure 8E:
Figure 9A:
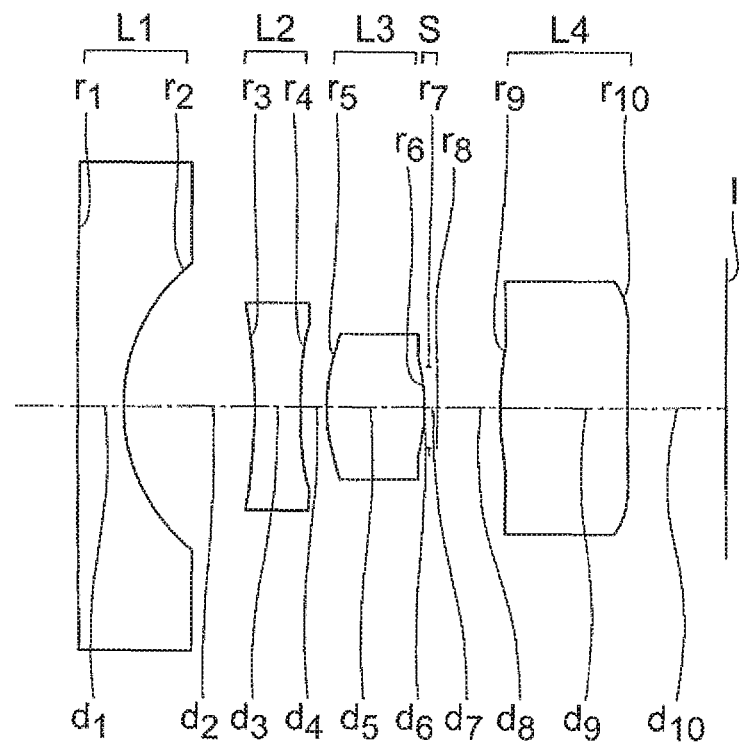
FIG. 9A, and FIG. 9B, FIG. 9C, FIG. 9D, and FIG. 9E are a cross-sectional view and aberration diagrams of an optical system of an example 9.
Figures 9B, 9C, 9D, 9E:
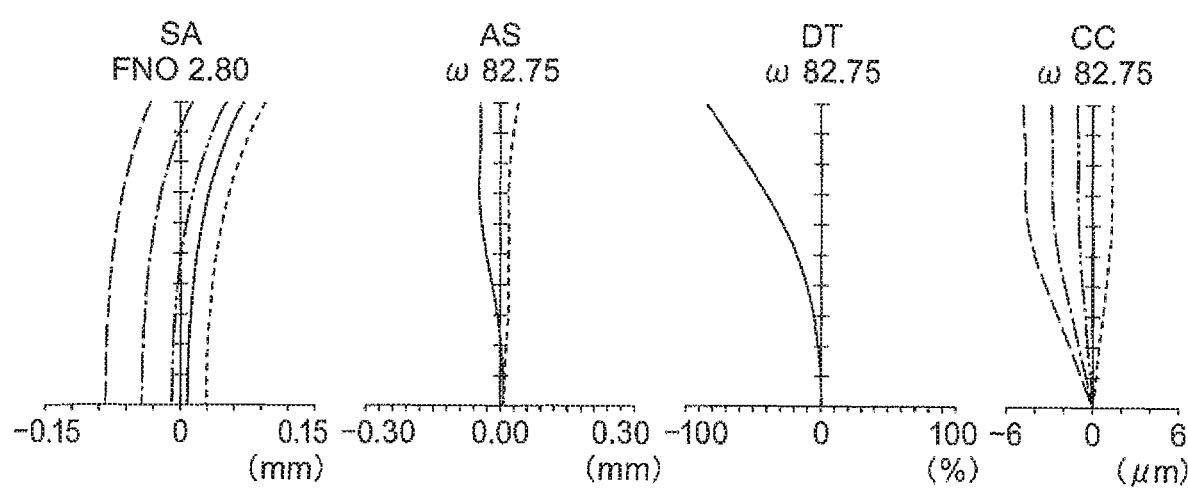
Figure 11A:
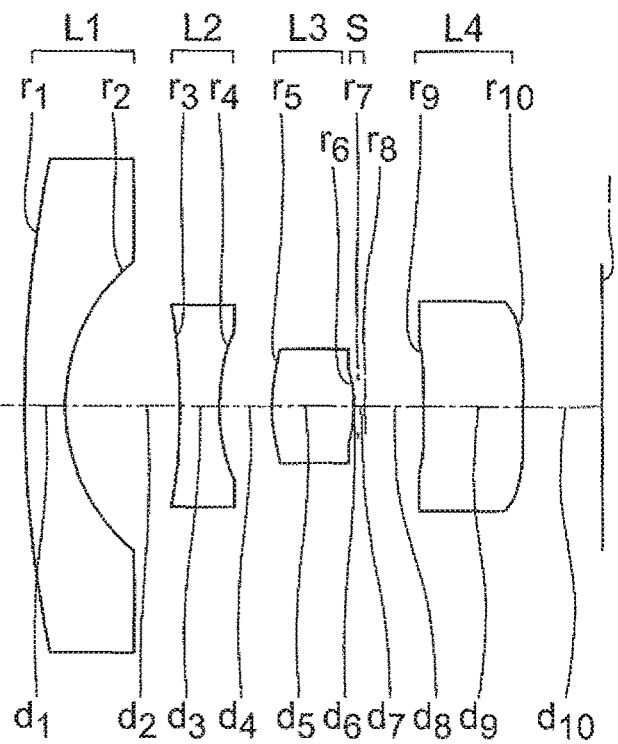
FIG. 11A, and FIG. 11B, FIG. 11C, FIG. 11D, and FIG. 11E are a cross-sectional view and aberration diagrams of an optical system of an example 11.
Figures 11B, 11C, 11D, 11E:
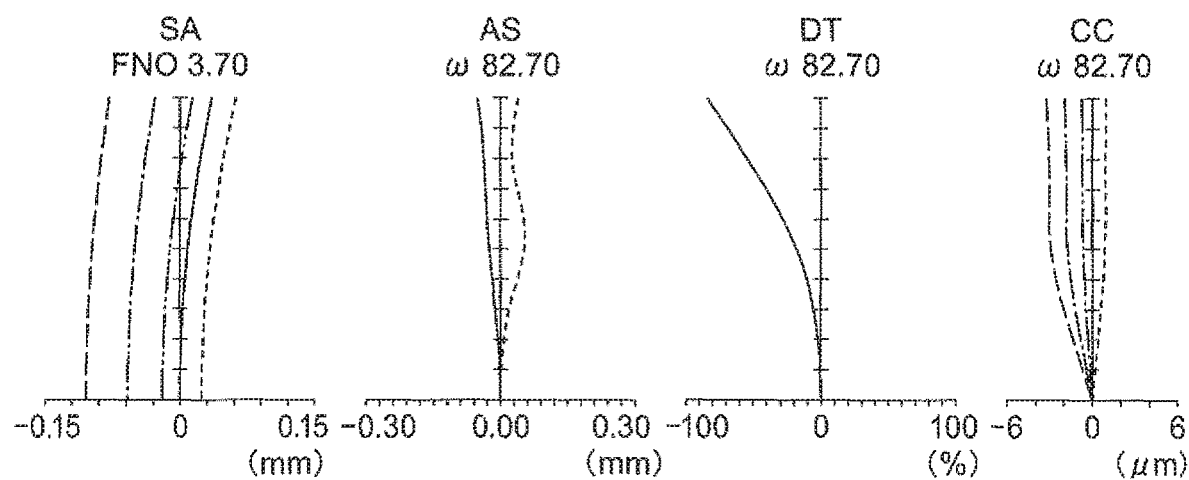
Figure 12A:
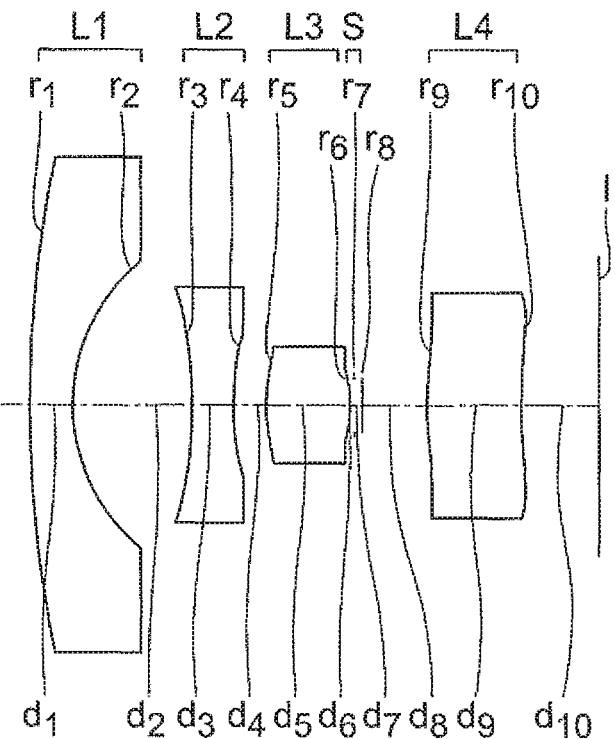
FIG. 12A, and FIG. 12B, FIG. 12C, FIG. 12D, and FIG. 12E are a cross-sectional view and aberration diagrams of an optical system of an example 12.
Figures 12B, 12C, 12D, 12E:
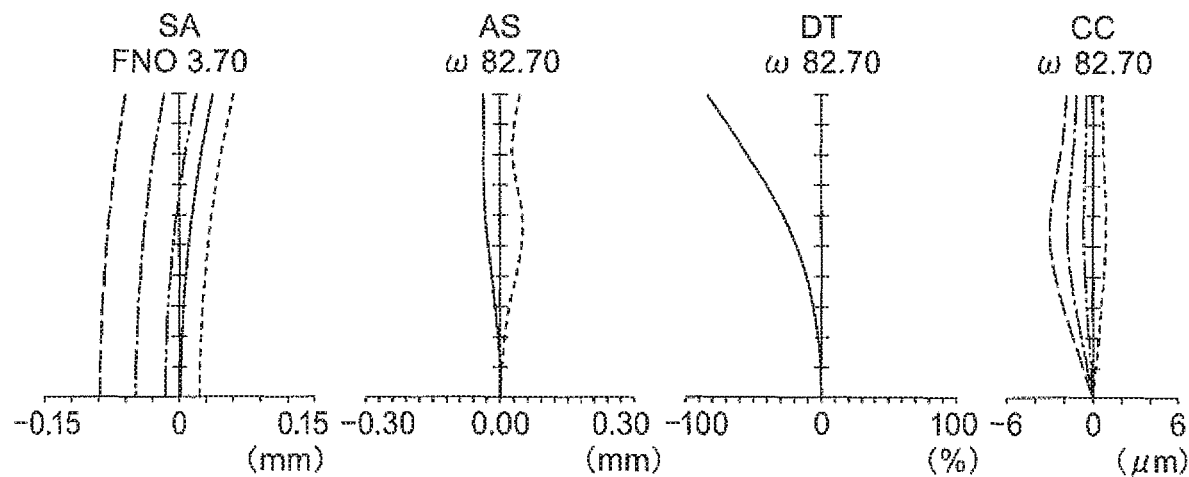
Figure 13A:
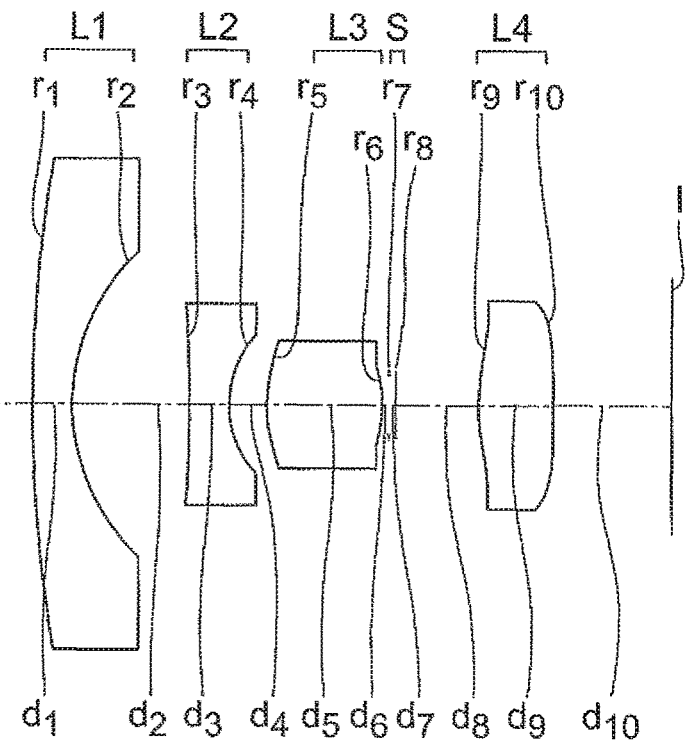
FIG. 13A, and FIG. 13B, FIG. 13C, FIG. 13D, and FIG. 13E are a cross-sectional view and aberration diagrams of an optical system of an example 13.
Figures 13B, 13C, 13D, 13E:
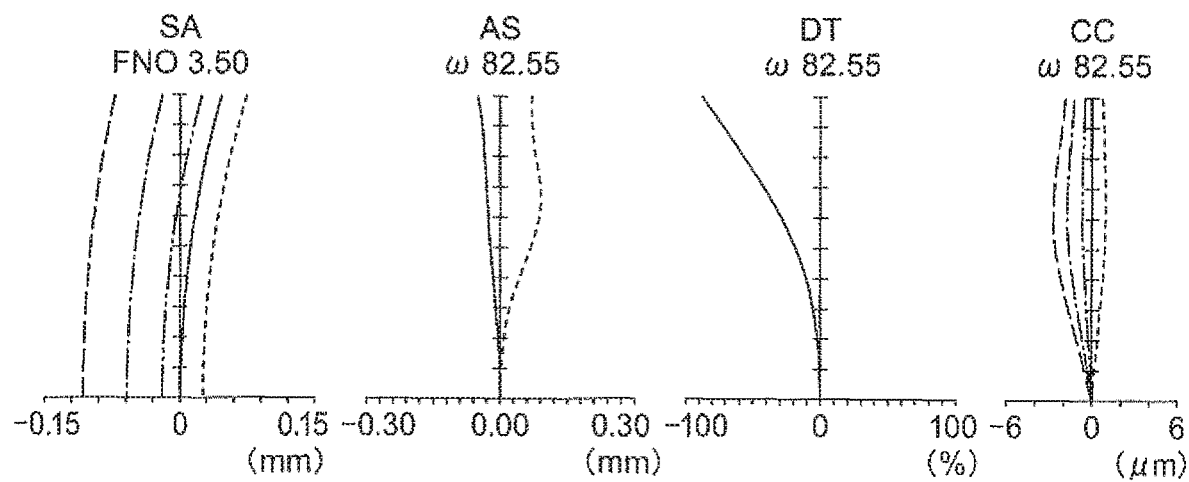
Figure 14A:
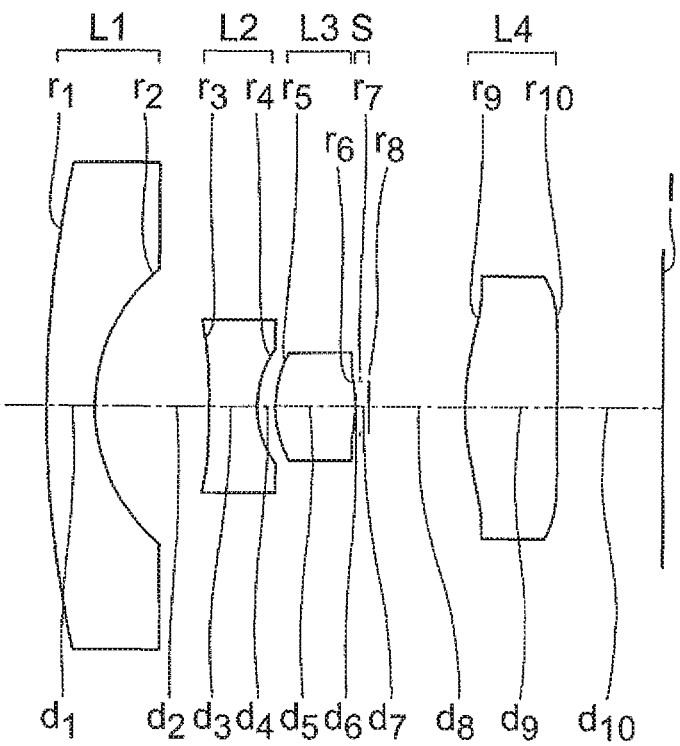
FIG. 14A, and FIG. 14B, FIG. 14C, FIG. 14D, and FIG. 14E are a cross-sectional view and aberration diagrams of an optical system of an example 14.
Figures 14B, 14C, 14D, 14E:
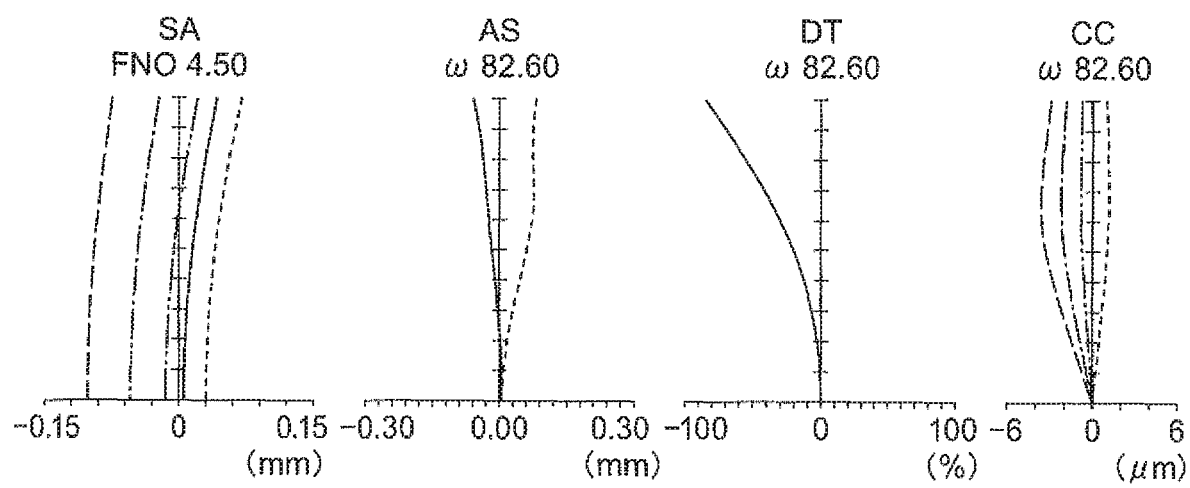
Figure 15A:
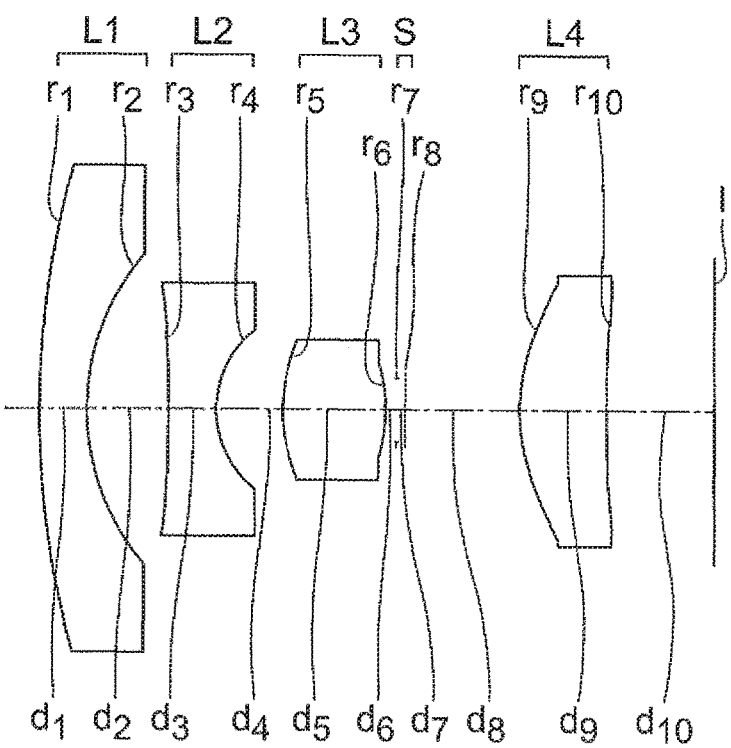
FIG. 15A, and FIG. 15B, FIG. 15C, FIG. 15D, and FIG. 15E are a cross-sectional view and aberration diagrams of an optical system of an example 15.
Figures 15B, 15C, 15D, 15E:
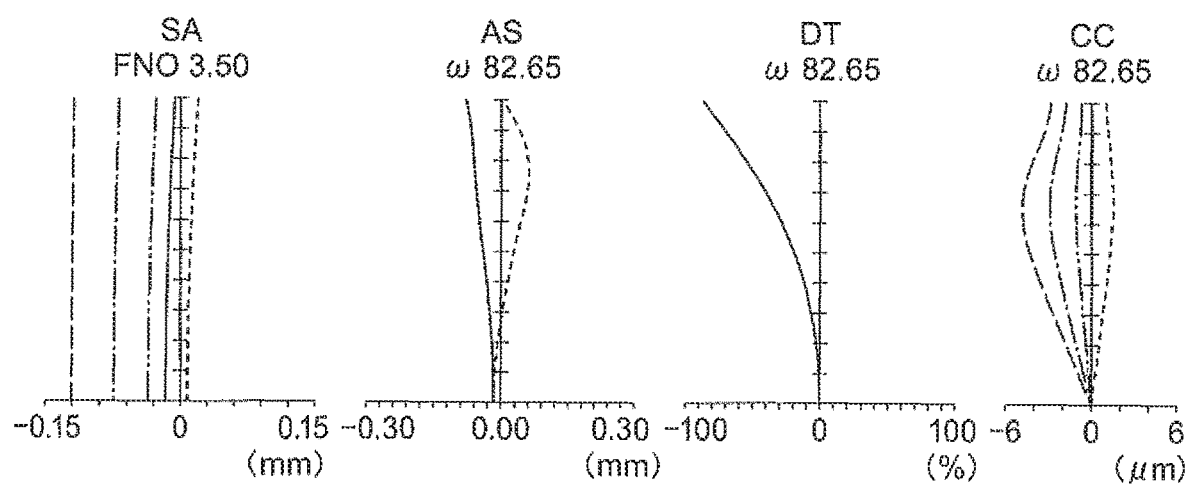

Prior to the explanation of examples, action and effect of embodiments according to certain aspects of the present invention will be described below. In the explanation of the action and effect of the embodiments concretely, the explanation will be made by citing concrete examples. However, similar to a case of the examples to be described later, aspects exemplified thereof are only some of the aspects included in the present invention, and there exists a large number of variations in these aspects. Consequently, the present invention is not restricted to the aspects that will be exemplified.

An image pickup apparatus of the present embodiment includes an optical system which includes a plurality of lenses and an aperture stop, and an image sensor which is disposed at an image position of the optical system, and the optical system includes in order from an object side, a first lens having a negative refractive power, a second lens having a negative refractive power, a third lens having a positive refractive power, and a fourth lens, and the following conditional expressions (1) and (3) are satisfied:

$$\alpha max - \alpha min < 4.0 \times 10^{-5}/° C. \quad (1), \text{ and}$$

$$0.2 < D1Ls/DsF < 3.0 \quad (3),$$

where,

α max denotes a largest coefficient of linear expansion among coefficients of linear expansion at 20 degrees of the plurality of lenses, α min denotes a smallest coefficient of linear expansion among the coefficients of linear expansion at 20 degrees of the plurality of lenses, D1Ls denotes a distance on an optical axis from an object-side surface of the first lens up to an object-side surface of the aperture stop, and DsF denotes a distance on the optical axis from an image-side surface of the aperture stop up to a lens surface positioned nearest to image.

In the optical system of the image pickup apparatus according to the present embodiment, a lens having a negative refractive power is used for the first lens and the second lens. Accordingly, it is possible to secure a wide angle of view.

In a case in which the first lens and the second lens are configured by a lens having a negative refractive power, a curvature of field and a chromatic aberration occur in two lenses. Therefore, by disposing a lens having a positive refractive power on the image side of the two lenses, the curvature of field and the chromatic aberration are corrected favorably.

Specifically, the third lens having a positive refractive power is disposed on the image side of the second lens. Accordingly, it is possible to correct the curvature of field and the chromatic aberration favorably.

Moreover, in the image pickup apparatus of the present embodiment, the abovementioned conditional expressions (1) and (3) are satisfied.

Conditional expression (1) is an expression in which a difference in the coefficient of linear expansion of the two lenses is taken. The coefficient of linear expansion is a coefficient of linear expansion at 20 degrees. The optical system of the present embodiment includes the plurality of lenses. In each of the plurality of lenses, a shape and a refractive index of lens varies with a change in temperature. Therefore, a focal length changes in each lens with the change in temperature.

Therefore, by satisfying conditional expression (1), it is possible to keep the focal length substantially constant as the overall optical system even when the focal length changes in each lens with the change in temperature. As a result, it is possible to suppress a fluctuation in aberration, and particularly a fluctuation in a spherical aberration and a fluctuation in a curvature of field. Moreover, it is possible to make a fluctuation in a focal position small.

By making an arrangement such that a value does not fall below a lower limit value of conditional expression (3), it is possible to suppress an increase in the refractive power of the first lens and an increase in the refractive power of the second lens while securing a wide angle of view and an appropriate back focus. As a result, it is possible to suppress further an increase in the negative distortion, and to suppress the curvature of field from occurring unduly.

By making an arrangement such that the value does not exceed an upper limit value of conditional expression (3), an increase in the distance from the object-side surface of the first lens up to the aperture stop is suppressed. Consequently, it is possible to make small a diameter of the first lens and a diameter of the second lens.

It is preferable that the following conditional expression (1') be satisfied instead of conditional expression (1).

$$1.00 \times 10^{-6}/° C. < \alpha max - \alpha min < 2.00 \times 10^{-5}/° C. \quad (1')$$

It is more preferable that the following conditional expression (1'') be satisfied instead of conditional expression $$1.00 \times 10^{-6}/° C. < \alpha max - \alpha min < 1.00 \times 10^{-5}/° C. \quad (1'')$$

It is more preferable that the following conditional expression (3') be satisfied instead of conditional expression (3).

$$0.70 < D1Ls/DsF < 2.70 \quad (3')$$

It is even more preferable that the following conditional expression (3'') be satisfied instead of conditional expression (3).

$$1.20 < D1Ls/DsF < 2.40 \quad (3'')$$

In such manner, the optical system of the image pickup apparatus according to the present embodiment, while being small-sized, has a wide angle of view and an appropriate back focus, and in which an off-axis aberration is corrected favorably, and a fluctuation in the focal length with respect to a temperature change is small. Consequently, according to the optical system of the image pickup apparatus of the present embodiment, an optical image with a high resolution and a wide angle of view is achieved stably, while being small-sized. Moreover, according to the image pickup apparatus of the present embodiment, it is possible to realize an image pickup apparatus equipped with an optical system which has a wide angle of view and an appropriate back focus, and in which an off-axis aberration is corrected favorably, and a fluctuation in the focal length with respect to the temperature change is small, while being small-sized.

In the image pickup apparatus of the present embodiment, it is preferable that the optical system include an aperture stop, and the following conditional expression (2) be satisfied:

$$0.1 < R1R/FL < 2.5 \quad (2),$$

where,

R1R denotes a paraxial radius of curvature of an image-side surface of the first lens, and FL denotes a focal length of the overall optical system.

Conditional expression (2) is a conditional expression related to a ratio of the paraxial radius of curvature of the image-side surface of the first lens and the focal length of the overall optical system. By satisfying conditional expression (2), it is possible to maintain a favorable optical performance.

By making an arrangement such that a value does not fall below a lower limit value of conditional expression (2), the negative refractive power at the image-side surface of the first lens does not become excessively large. As a result, it is possible to suppress further an increase in a negative distortion, and to suppress a curvature of field from occurring unduly.

Moreover, when the value falls below the lower limit value of conditional expression (2), a radius of curvature at the image-side surface of the first lens becomes small. In this case, a thickness of a lens at periphery (hereinafter, referred to as 'peripheral thickness') becomes thick, or, a ratio of a thickness of a lens at center and a thickness of the lens at periphery (hereinafter, referred to as 'thickness ratio') becomes large. By making an arrangement such that the value does not fall below the lower limit value of conditional expression (2), it is possible to suppress an increase in the peripheral thickness and an increase in the thickness ratio. As a result, it is possible to maintain workability of the first lens favorably.

By making an arrangement such that the value does not exceed an upper limit value of conditional expression (2), it is possible to maintain the radius of curvature at the image-side surface of the first lens to be appropriate. Consequently, it is possible to suppress a further increase in the distortion and an occurrence of a coma, while securing a wide angle of view and an appropriate back focus.

When the value exceeds the upper limit value of conditional expression (2), the negative refractive power at the image-side surface of the first lens becomes small. In this case, for securing the wide angle of view and the appropriate back focus, it is necessary either to make the negative refractive power at an object-side surface of the first lens large, or to make the negative refractive power of the second lens large.

However, when the negative refractive power at the object-side surface of the first lens is made large, the negative distortion increases further. Moreover, when the negative refractive power at the second lens is made large, the coma occurs substantially. Therefore, it is desirable to make the arrangement such that the value does not exceed the upper limit value of conditional expression (2).

It is preferable that the following conditional expression (2') be satisfied instead of conditional expression (2).

$$0.50 < R1R/FL < 2.40 \quad (2')$$

It is more preferable that the following conditional expression (2") be satisfied instead of conditional expression (2).

$$0.90 < R1R/FL < 2.30 \quad (2'')$$

In the image pickup apparatus of the present embodiment, it is preferable that the following conditional expression (4) be satisfied:

$$-0.01 < FL/R1L < 1.0 \quad (4),$$

where,

R1L denotes a paraxial radius of curvature of an object-side surface of the first lens, and FL denotes the focal length of the overall optical system.

It is possible to make the refractive power at the object-side surface of the first lens to be any of a negative refractive power and a positive refractive power.

In a case of letting the refractive power at the object-side surface of the first lens to be the negative refractive power, an arrangement is to be made such that a value does not fall below a lower limit value of conditional expression (4). By making such arrangement, the negative refractive power at the object-side surface of the first lens does not become excessively large. As a result, it is possible to suppress the negative distortion from increasing further.

In a case of letting the refractive power at the object-side surface of the first lens to be the positive refractive power, an arrangement is to be made such that the value does not exceed an upper limit value of conditional expression (4). By making such arrangement, the positive refractive power at the object-side surface of the first lens does not become excessively large. As a result, it is possible to make the diameter of the first lens small, and to secure a favorable workability of the first lens.

For securing a wide angle of view and an appropriate back focus, it is necessary to make the focal length of the first lens appropriate. When the value exceeds the upper limit value of conditional expression (4), the positive refractive power at the object-side surface of the first lens becomes excessively large. Therefore, for securing an appropriate negative focal length at the first lens, it is necessary to make the refractive power at the image-side surface of the first lens large. However, when the refractive power at the image-side surface of the first lens is made large, the workability of the first lens is deteriorated.

Moreover, when the positive refractive power at the object-side surface of the first lens becomes excessively large, the negative refractive power in the first lens becomes excessively small. In this case, for securing a wide angle of view and an appropriate back focus, it is necessary to make a distance between the first lens and the second lens long. However, when the distance between the first lens and the second lens is made long, the diameter of the first lens becomes large. Therefore, it is desirable to make an arrangement such that the value does not exceed the upper limit value of conditional expression (4).

It is more preferable that the following conditional expression (4') be satisfied instead of conditional expression (4).

$$0.00 < FL/R1L < 0.70 \quad (4')$$

It is even more preferable that the following conditional expression (4") be satisfied instead of conditional expression (4).

$$0.005 < FL/R1L < 0.40 \quad (4'')$$

In the image pickup apparatus of the present embodiment, it is preferable that the following conditional expression (5) be satisfied:

$$0.1 < R2R/FL < 50 \tag{5}$$

where,

R2R denotes a paraxial radius of curvature of an image-side surface of the second lens, and FL denotes the focal length of the overall optical system.

By making an arrangement such that a value does not fall below a lower limit value of conditional expression (5), the negative refractive power at the image-side surface of the second lens does not become excessively large. As a result, it is possible to suppress the negative distortion from increasing further, and also to suppress the curvature of field from occurring unduly.

When the value falls below the lower limit value of conditional expression (5), a radius of curvature of the image-side surface of the second lens becomes small. Consequently, there is an increase in the peripheral thickness and an increase in the thickness ratio. By making an arrangement such that the value does not fall below the lower limit value of conditional expression (5), it is possible to suppress the increase in the peripheral thickness and the increase in the thickness ratio. As a result, it is possible to maintain the workability of the second lens to be favorable.

By making an arrangement such that the value does not exceed an upper limit value of conditional expression (5), it is possible to secure appropriately the radius of curvature of the image-side surface of the second lens. As a result, it is possible to suppress the distortion from increasing further and an occurrence of the coma while securing a wide angle of view and an appropriate back focus.

When the value exceeds the upper limit value of conditional expression (5), the negative refractive power at the image-side surface of the second lens becomes excessively small. In this case, for securing a wide angle of view and an appropriate back focus, it is necessary either to make the negative refractive power at the object-side surface of the second lens excessively large or to make the negative refractive power of the first lens excessively large.

However, when the negative refractive power at the object-side surface of the second lens is made excessively large, the coma occurs substantially. Moreover, when the negative refractive power of the first lens is made excessively large, the negative distortion increases further. Therefore, it is desirable to make an arrangement such that the value does not exceed the upper limit value of conditional expression (5).

It is more preferable that the following conditional expression (5') be satisfied instead of conditional expression (5).

$$0.30 < R2R/FL < 40.00 \tag{5'}$$

It is even more preferable that the following conditional expression (5") be satisfied instead of conditional expression (5).

$$0.50 < R2R/FL < 30.00 \tag{5"}$$

In the image pickup apparatus of the present embodiment, it is preferable that the following conditional expression (6) is satisfied:

$$-1.0 < FL/R2L < 0.8 \tag{6}$$

where,

R2L denotes a paraxial radius of curvature of an object-side surface of the second lens, and FL denotes the focal length of the overall optical system.

It is possible to make the refractive power at the object-side surface of the second lens to be any of the negative refractive power and the positive refractive power.

In a case of letting the refractive power at the object-side surface of the second lens to be the negative refractive power, an arrangement is to be made such that a value does not fall below a lower limit value of conditional expression (6). By making such arrangement, the negative refractive power at the object-side surface of the second lens does not become excessively large. As a result, it is possible to suppress the negative distortion from increasing further.

In a case of letting the refractive power at the object-side surface of the second lens to be the positive refractive power, an arrangement is to be made such that the value does not exceed an upper limit value of conditional expression (6). By making such arrangement, the positive refractive power at the object-side surface of the second lens does not become excessively large. Asa result, it is possible to make the diameter of the second lens small, and to secure a favorable workability of the second lens.

For securing a wide angle of view and an appropriate back focus, it is necessary to make the focal length of the second lens appropriate. When the value exceeds the upper limit value of conditional expression (6), the positive refractive power at the object-side surface of the second lens becomes excessively large. For securing an appropriate negative focal length at the second lens, it is necessary to make the refractive power at the image-side surface of the second lens large. However, when the refractive power of the image-side surface of the second lens is made large, the workability of the second lens is deteriorated.

Moreover, when the positive refractive power at the object-side surface of the second lens becomes excessively large, the negative refractive power in the second lens becomes excessively small. In this case, for securing a wide angle of view and an appropriate back focus, it is necessary to make a distance between the second lens and the third lens long. However, when the distance between the second lens and the third lens is made long, the diameter of the second lens becomes large. Therefore, it is desirable to make an arrangement such that the value does not exceed the upper limit value of conditional expression (6).

It is more preferable that the following conditional expression (6') be satisfied instead of conditional expression (6).

$$-0.90 < FL/R2L < 0.60 \tag{6'}$$

It is even more preferable that the following conditional expression (6") be satisfied instead of conditional expression (6).

$$-0.80 < FL/R2L < 0.40 \tag{6"}$$

In the image pickup apparatus of the present embodiment, it is preferable that the following conditional expression (7) be satisfied:

$$0.5 < \Phi 1L/IH < 3.0 \tag{7}$$

where,

IH denotes α maximum image height, and

Φ1L denotes an effective aperture at the object-side surface of the first lens.

Conditional expression (7) is a conditional expression related to a ratio of the maximum image height and the effective aperture at the first lens. By satisfying conditional expression (7), it is possible to make the optical system small-sized.

By making an arrangement such that a value does not fall below a lower limit value of conditional expression (7), in the first lens, it is possible to separate a position through which an axial light beam passes and a position through which an off-axis light beam passes. As a result, it is possible to correct the curvature of field favorably. By making an arrangement such that the value does not exceed an upper limit value of conditional expression (7), it is possible to suppress the diameter of the first lens to be small. As a result, it is possible to make the optical system small-sized.

It is more preferable that the following conditional expression (7') be satisfied instead of conditional expression (7).

$$0.80<\Phi 1L/IH<2.70 \tag{7'}$$

It is even more preferable that the following conditional expression (7") be satisfied instead of conditional expression (7).

$$0.10<\Phi 1L/IH<2.40 \tag{7"}$$

In the image pickup apparatus of the present embodiment, it is preferable that the optical system include a lens surface positioned nearest to object and a lens surface positioned nearest to image, and the following conditional expression (8) be satisfied:

$$0.05<D1R2L/\Sigma d<0.5 \tag{8},$$

where,

D1R2L denotes an air space from the image-side surface of the first lens up to the object-side surface of the second lens, and Σd denotes a distance from the lens surface positioned nearest to object up to the lens surface positioned nearest to image.

By making an arrangement such that a value does not fall below a lower limit value of conditional expression (8), it is possible to secure an appropriate back focus, as well as to realize widening of the angle of view. Moreover, in the first lens, it is possible to separate the position through which the axial light beam passes and the position through which the off-axis light beam passes. As a result, it is possible to correct the curvature of field favorably.

By making an arrangement such that the value does not exceed an upper limit value of conditional expression (8), it is possible to secure a thickness of each lens appropriately, as well as to make the diameter of the first lens small.

When the value exceeds the upper limit value of conditional expression (8), the distance between the first lens and the second lens becomes long. In this case, it is possible make the negative refractive power in the first lens small, but the diameter of the first lens becomes large. Therefore, it is desirable to make an arrangement such that the value exceeds the upper limit value of conditional expression (8).

It is more preferable that the following conditional expression (8') be satisfied instead of conditional expression (8).

$$0.07<D1R2L/\Sigma d<0.40 \tag{8'}$$

It is even more preferable that the following conditional expression (8") be satisfied instead of conditional expression (8).

$$0.10<D1R2L/\Sigma d<0.30 \tag{8"}$$

In the image pickup apparatus of the present embodiment, it is preferable that the optical system include a lens surface positioned nearest to object and a lens surface positioned nearest to image, and the following conditional expression (9) be satisfied:

$$0.01<D2R3L/\Sigma d<0.3 \tag{9},$$

where,

D2R3L denotes an air space from the image-side surface of the second lens up to an object-side surface of the third lens, and Σd denotes the distance from the lens surface positioned nearest to object up to the lens surface positioned nearest to image.

By making an arrangement such that a value does not fall below a lower limit value of conditional expression (9), it is possible to secure an appropriate back focus, as well as to realize widening of the angle of view. Moreover, in the second lens, it is possible to separate a position through which an axial light beam passes and a position through which an off-axis light beam passes. As a result, it is possible correct the curvature of field favorably.

By making an arrangement such that the value does not exceed an upper limit value of conditional expression (9), it is possible to maintain a difference in the position through which the axial light beam passes and a position through which the off-axis light beam passes to be appropriate. Consequently, in the third lens, it is possible to correct a chromatic aberration of magnification favorably.

When the value exceeds the upper limit value of conditional expression (9), the distance between the second lens unit and the third lens unit becomes long. In this case, since the difference in the position through which the axial light beam passes and the position through which the off-axis light beam passes becomes small, both of an axial aberration and an off-axis aberration cannot be corrected favorably. Therefore, it is desirable to make an arrangement such that the value exceeds the upper limit value of conditional expression (9).

It is more preferable that the following conditional expression (9') be satisfied instead of conditional expression (9).

$$0.02<D2R3L/\Sigma d<0.25 \tag{9'}$$

It is even more preferable that the following conditional expression (9") be satisfied instead of conditional expression (9).

$$0.03<D2R3L/\Sigma d<0.20 \tag{9"}$$

In the image pickup apparatus of the present embodiment, it is preferable that the optical system include a lens surface positioned nearest to object and a lens surface positioned nearest to image, and the following conditional expression (10) be satisfied:

$$0.05<D3R4L/\Sigma d<0.5 \tag{10},$$

where,

D3R4L denotes an air space from an image-side surface of the third lens up to an object-side surface of the fourth lens, and Σd denotes the distance from the lens surface positioned nearest to object up to the lens surface positioned nearest to image.

By making an arrangement such that a value does not fall below a lower limit value of conditional expression (10), in the fourth lens, it is possible to separate a position through which the axial light beam passes and a position through which the off-axis light beam passes. As a result, it is possible to correct the curvature of field favorably.

In a case where the aperture stop is disposed between the third lens and the fourth lens, it is possible to separate further the position through which the axial light beam passes and the position through which the off-axis light beam passes. As a result, it is possible to correct the curvature of field favorably.

By making an arrangement such that the value does not exceed an upper limit value of conditional expression (10), it is possible to secure the thickness of each lens to be appropriate. As a result, it is possible to maintain the workability of each lens to be favorable. Moreover, by making an arrangement such that the value does not exceed the upper limit value of conditional expression (10), it is possible to maintain the distance between the third lens and the fourth lens to be appropriate. Accordingly, in the fourth lens, it is possible to separate a position through which the axial light beam passes and a position through which the off-axis light beam passes. As a result, it is possible to correct the curvature of field favorably.

It is more preferable that the following conditional expression (10') be satisfied instead of conditional expression (10).

$$0.07 < D3R4L/\Sigma d < 0.40 \quad (10')$$

It is even more preferable that the following conditional expression (10") be satisfied instead of conditional expression (10).

$$0.09 < D3R4L/\Sigma d < 0.30 \quad (10'')$$

In the image pickup apparatus of the present embodiment, it is preferable that the following conditional expression (11) be satisfied:

$$-10.0 < f1/FL < -0.5 \quad (11),$$

where, f1 denotes a focal length of the first lens, and

FL denotes the focal length of the overall optical system.

By making an arrangement such that a value does not fall below a lower limit value of conditional expression (11), it is possible to correct the curvature of field favorably, as well as to suppress an increase in the diameter of the first lens.

When the value falls below the lower limit value of conditional expression (11), the negative refractive power in the first lens becomes excessively small. In this case, for securing a wide angle of view and an appropriate back focus, it is necessary either to make the negative refractive power in the second lens large, or to make the distance between the first lens and the second lens long.

However, when the negative refractive power in the second lens is made large, the curvature of field occurs unduly substantially. Moreover, when the distance between the first lens and the second lens is made long, the lens becomes large-sized. Therefore, it is desirable to make an arrangement such that the value does not fall below the lower limit value of conditional expression (11).

By making an arrangement such that the value does not exceed an upper limit value of conditional expression (11), it is possible to suppress an increase in the curvature of field. When the value exceeds the upper limit value of conditional expression (11) is exceeded, the negative refractive power in the first lens becomes excessively large. As a result, the curvature of field occurs unduly substantially. Therefore, it is desirable to make an arrangement such that the value does not exceed the upper limit value of conditional expression (11).

By making an arrangement such that the value does not exceed the upper limit value of conditional expression (11), the radius of curvature of the first lens does not become excessively small. Consequently, it is possible to maintain the workability of the first lens favorably.

It is more preferable that the following conditional expression (11') be satisfied instead of conditional expression (11).

$$-8.00 < f1/FL < -1.00 \quad (11')$$

It is even more preferable that the following conditional expression (11") be satisfied instead of conditional expression (11).

$$-6.00 < f1/FL < -1.50 \quad (11'')$$

In the image pickup apparatus of the present embodiment, it is preferable that the following conditional expression (12) be satisfied:

$$-10.0 < f2/FL < -0.1 \quad (12),$$

where, f2 denotes a focal length of the second lens, and

FL denotes the focal length of the overall optical system.

By making an arrangement such that a value does not fall below a lower limit value of conditional expression (12), it is possible to correct the curvature of field favorably, as well as to suppress an increase in the diameter of the second lens.

When the value falls below the lower limit value of conditional expression (12), the negative refractive power in the second lens becomes excessively small. In this case, for securing a wide angle of view and an appropriate back focus, it is necessary to make either the negative refractive power of the first lens large, or to make the distance between the second lens and the third lens long.

However, when the negative refractive power of the first lens is made excessively large, the curvature of field occurs unduly substantially. Moreover, when the distance between the second lens and the third lens is made long, the lens becomes large-sized. Therefore, it is desirable to make an arrangement such that the value does not fall below the lower limit value of conditional expression (12).

By making an arrangement such that the value does not exceed an upper limit value of conditional expression (12), it is possible to suppress an increase in the curvature of field. When the value exceeds the upper limit value of conditional expression (12), the negative refractive power of the second lens becomes excessively large. As a result, the curvature of field occurs unduly substantially. Therefore, it is desirable to make an arrangement such that the value does not exceed the upper limit value of conditional expression (12).

By making an arrangement such that the value does not exceed the upper limit value of conditional expression (12), since the radius of curvature of the second lens does not become excessively small, it is possible to maintain the workability of the second lens to be favorable.

It is more preferable that the following conditional expression (12') be satisfied instead of conditional expression (12).

$$-8.00 < f2/FL < -0.50 \quad (12')$$

It is even more preferable that the following conditional expression (12") be satisfied.

$$-6.00 < f2/FL < -0.80 \quad (12'')$$

In the image pickup apparatus of the present embodiment, it is preferable that the following conditional expression (13) be satisfied:

$$0.5 < f3/FL < 20.0 \quad (13),$$

where, f3 denotes a focal length of the third lens, and

FL denotes the focal length of the overall optical system.

By satisfying conditional expression (13), it is possible to correct the coma and the chromatic aberration of magnification favorably.

By making an arrangement such that a value does not fall below a lower limit value of conditional expression (13), the positive refractive power of the third lens does not become excessively large. Consequently, it is possible to correct the coma favorably. By making an arrangement such that the value does not exceed an upper limit value of conditional expression (13), the positive refractive power of the third lens does not become excessively small. Consequently, it is possible to correct the chromatic aberration of magnification favorably.

By disposing the third lens on the object side of the aperture stop, and satisfying conditional expression (13), it is possible to correct the coma and the chromatic aberration of magnification more favorably.

It is more preferable that the following conditional expression (13') be satisfied instead of conditional expression (13).

$$0.60 < f3/FL < 12.00 \tag{13'}$$

It is even more preferable that the following conditional expression (13") be satisfied instead of conditional expression (13).

$$0.70 < f3/FL < 4.00 \tag{13''}$$

In the image pickup apparatus of the present embodiment, it is preferable that the optical system include a lens surface positioned nearest to object and a lens surface positioned nearest to image, and the following conditional expression (14) be satisfied:

$$2.0 < \Sigma d/FL < 8.0 \tag{14}$$

where,

Σd denotes the distance from the lens surface positioned nearest to object up to the lens surface positioned nearest to image, and FL denotes the focal length of the overall optical system.

Conditional expression (14) is a conditional expression related to a ratio of the total length of the optical system and the focal length of the overall optical system. By satisfying conditional expression (14), it is possible to correct various aberrations favorably, as well as to achieve small-sizing and widening of the angle of view of the optical system.

By making an arrangement such that a value does not fall below a lower limit value of conditional expression (14), it is possible to prevent a distance between the lenses from becoming narrow. Accordingly, since it is possible to maintain a distance between the lenses to be appropriate, it is possible to separate a position through which the axial light beam passes and a position through which the off-axis light beam passes in the first lens and the fourth lens in particular. As a result, it is possible to correct the curvature of field favorably, and moreover, it is possible to prevent further increase in the distortion.

By making an arrangement such that the value does not exceed an upper limit value of conditional expression (14), it is possible to maintain the distance between the lenses to be appropriate, as well as to make a diameter of each lens small, even when the angle of view is widened.

It is more preferable that the following conditional expression (14') be satisfied instead of conditional expression (14).

$$2.70 < \Sigma d/FL < 6.00 \tag{14'}$$

It is even more preferable that the following conditional expression (14") be satisfied instead of conditional expression (14).

$$3.40 < \Sigma d/FL < 5.50 \tag{14''}$$

In the image pickup apparatus of the present embodiment, it is preferable that the following conditional expression (15) is satisfied:

$$0.8 < vd1/vd3 < 3.5 \tag{15}$$

where, vd1 denotes Abbe number for the first lens, and vd3 denotes Abbe number for the third lens.

By making an arrangement such that a value does not fall below a lower limit value of conditional expression (15), it is possible to correct the chromatic aberration of magnification favorably. By making an arrangement such that the value does not exceed an upper limit value of conditional expression (15), it is possible to correct the longitudinal chromatic aberration favorably.

It is more preferable that the following conditional expression (15') be satisfied instead of conditional expression (15).

$$0.85 < vd1/vd3 < 3.20 \tag{15'}$$

It is even more preferable that the following conditional expression (15") be satisfied instead of conditional expression (15).

$$0.90 < vd1/vd3 < 2.90 \tag{15''}$$

In the image pickup apparatus of the present embodiment, it is preferable that the following conditional expression (16) be satisfied:

$$0.8 < vd2/vd3 < 3.5 \tag{16}$$

where, vd2 denotes Abbe number for the second lens, and vd3 denotes the Abbe number for the third lens.

By making an arrangement such that a value does not fall below a lower limit value of conditional expression (16), it is possible to correct the chromatic aberration of magnification favorably. By making an arrangement such that the value does not exceed an upper limit value of conditional expression (16), it is possible to correct the longitudinal chromatic aberration favorably.

It is more preferable that the following conditional expression (16') be satisfied instead of conditional expression (16).

$$1.00 < vd2/vd3 < 3.20 \tag{16'}$$

It is even more preferable that the following conditional expression (16") is satisfied instead of conditional expression (16).

$$1.20 < vd2/vd3 < 2.90 \tag{16''}$$

In the image pickup apparatus of the present embodiment, it is preferable that the following conditional expression (17) be satisfied:

$$0.3 < vd3/vd4 < 0.8 \tag{17}$$

where, vd3 denotes the Abbe number for the third lens, and vd4 denotes Abbe number for the fourth lens.

By making an arrangement such that a value does not fall below a lower limit value of conditional expression (17), it is possible to correct the chromatic aberration of magnification favorably. By making an arrangement such that the value does not exceed an upper limit value of conditional expression (17), it is possible correct the longitudinal chromatic aberration favorably.

It is more preferable that the following conditional expression (17') be satisfied instead of conditional expression (17).

$$0.32 < vd3/vd4 < 0.70 \quad (17')$$

It is even more preferable that the following conditional expression (17") be satisfied instead of conditional expression (17).

$$0.34 < vd3/vd4 < 0.60 \quad (17")$$

In the image pickup apparatus of the present embodiment, it is preferable that the following conditional expression (18) be satisfied:

$$-1.0 < f1/R1L < 0 \quad (18),$$

where, f1 denotes the focal length of the first lens, and

R1L denotes the paraxial radius of curvature of the object-side surface of the first lens.

By making an arrangement such that a value does not fall below a lower limit value of conditional expression (18), since the positive refractive power at the object-side surface of the first lens does not become excessively large, it is possible to suppress an increase in the negative refractive power at the image-side surface of the first lens. Consequently, it is possible suppress an occurrence of an astigmatism. Moreover, since it is possible to suppress an increase in the peripheral thickness of the first lens, it is possible to maintain the workability of the first lens to be favorable.

By making an arrangement such that the value does not exceed an upper limit value of conditional expression (18), it is possible to suppress a large refraction of an off-axis principal light ray which is incident on the object-side surface of the first lens. Consequently, it is possible to suppress further increase in the negative distortion in particular.

It is more preferable that the following conditional expression (18') be satisfied instead of conditional expression (18).

$$-0.90 < f1/R1L < -0.001 \quad (18')$$

It is even more preferable that the following conditional expression (18") be satisfied instead of conditional expression (18).

$$-0.75 < f1/R1L < -0.010 \quad (18")$$

In the image pickup apparatus of the present embodiment, it is preferable that the following conditional expression (19) be satisfied:

$$-1.0 < f2/R2L < 3.0 \quad (19),$$

where, f2 denotes the focal length of the second lens, and

R2L denotes the paraxial radius of curvature of the object-side surface of the second lens.

It is possible to make the refractive power at the object-side surface of the second lens to be any of the negative refractive power and the positive refractive power.

In a case of letting the refractive power at the object-side surface of the second lens to be the positive refractive power, an arrangement is to be made such that a value does not fall below a lower limit value of conditional expression (19). By making such arrangement, since the positive refractive power at the object-side surface of the second lens does not become excessively large, it is possible to suppress an increase in the negative refractive power at the image-side surface of the second lens. Consequently, it is possible to suppress an occurrence of the astigmatism. Moreover, since it is possible to suppress an increase in the peripheral thickness, it is possible to maintain the workability of the second lens to be favorable.

In a case of letting the refractive power at the object-side surface of the second lens to be the negative refractive power, an arrangement is to be made such that the value does not exceed an upper limit value of conditional expression (19). By making such arrangement, it is possible to suppress a large refraction of an off-axis principal light ray incident on the object-side surface of the second lens. Consequently, it is possible to suppress further increase in the negative distortion in particular.

It is more preferable that the following conditional expression (19') be satisfied instead of conditional expression (19).

$$-0.80 < f2/R2L < 2.70 \quad (19')$$

It is even more preferable that the following conditional expression (19") be satisfied instead of conditional expression (19).

$$-0.60 < f2/R2L < 2.40 \quad (19")$$

In the image pickup apparatus of the present embodiment, it is preferable that the following conditional expression (20) be satisfied:

$$-1.0 < (R3L+R3R)/(R3L-R3R) < 0.5 \quad (20),$$

where,

R3L denotes a paraxial radius of curvature of the object-side surface of the third lens, and R3R denotes a paraxial radius of curvature of the image-side surface of the third lens.

By satisfying conditional expression (20), it is possible to correct a spherical aberration and the coma favorably.

It is more preferable that the following conditional expression (20') be satisfied instead of conditional expression (20).

$$-0.80 < (R3L+R3R)/(R3L-R3R) < 0.40 \quad (20')$$

It is even more preferable that the following conditional expression (20") be satisfied instead of conditional expression (20).

$$-0.60 < (R3L+R3R)/(R3L-R3R) < 0.30 \quad (20")$$

In the image pickup apparatus of the present embodiment, it is preferable that the optical system include a lens surface positioned nearest to object and a lens surface positioned nearest to image, and the following conditional expression (21) be satisfied:

$$2.0 < \Sigma d/D\text{maxair} < 9.0 \quad (21),$$

where, $\Sigma d$ denotes the distance from the lens surface positioned nearest to object up to the lens surface positioned nearest to image, and Dmaxair denotes a largest air space among air spaces between the lens surface positioned nearest to object and the lens surface positioned nearest to image.

The air space is a space between the two adjacent lenses. Moreover, in a case in which the aperture stop is positioned between the two adjacent lenses, the air space is a space between the lens and the aperture stop.

By making an arrangement such that a value does not fall below a lower limit value of conditional expression (21), it is possible to keep a thickness of a lens appropriately. As a result, it is possible to make a workability of a lens favorable. By making an arrangement such that the value does not exceed an upper limit value of conditional expression (21), it is possible to suppress the increase in the total length of the optical system. As a result, it is possible to make the optical system small-sized.

Moreover, when the distance between the first lens and the second lens corresponds to Dmaxair, the distance between the first lens and the second lens can be secured to be adequately wide. Consequently, in the first lens, it is possible to separate the position through which an axial light beam passes and the position through which an off-axis light beam passes. As a result, it is possible to correct favorably, an off-axis aberration, and particularly the curvature of field, and moreover, it is possible to prevent the distortion from increasing further.

In such manner, it is preferable to make an arrangement such that the distance between the first lens and the second lens corresponds to Dmaxair. Moreover, an arrangement may be made such that the distance between the second lens and the third lens corresponds to Dmaxair. In this case, since a combined focal length of the second lens and the third lens does not become excessively large, it is possible to achieve both of small-sizing and widening of the angle of view of the optical system.

It is more preferable that the following conditional expression (21') be satisfied instead of conditional expression (21).

$$2.50<\Sigma d/D\text{maxair}<8.00 \quad (21')$$

It is even more preferable that the following conditional expression (21") be satisfied instead of conditional expression (21).

$$3.00<\Sigma d/D\text{maxair}<7.00 \quad (21")$$

In the image pickup apparatus of the present embodiment, it is preferable that the optical system include an aperture stop, and the following conditional expression (22) be satisfied:

$$1.0<D1Ls/FL<5.0 \quad (22),$$

where,

D1Ls denotes the distance on the optical axis from the object-side surface of the first lens up to an object-side surface of the apertures stop, and FL denotes the focal length of the overall optical system.

By exceeding a lower limit value of conditional expression (22), it is possible to move away the aperture stop from the object-side surface of the first lens. Accordingly, at the first lens, it is possible to separate a position through which an axial light beam passes and a position through which an off-axis light beam passes. As a result, it is possible to correct both of an axial aberration and an off-axis aberration favorably. By falling below an upper limit value of conditional expression (22), it is possible to suppress a distance from the first lens up to the aperture stop, to be short. As a result, it is possible to shorten the total length of the optical system.

It is more preferable that the following conditional expression (22') be satisfied instead of conditional expression (22).

$$1.50<D1Ls/FL<4.50 \quad (22')$$

It is even more preferable that the following conditional expression (22") be satisfied instead of conditional expression (22).

$$2.00<D1Ls/FL<4.00 \quad (22")$$

In the image pickup apparatus of the present embodiment, it is preferable that the half angle of view be not less than 65 degrees.

By making such arrangement, it is possible to capture a wide range.

It is preferable that the image pickup apparatus of the present embodiment include an optical member through which light passes, on the object side of the optical system, and both surfaces of the optical member be curved surfaces.

It is possible to form two spaces by the optical member. For instance, a closed space is formed by the optical member and another member, and the optical system is disposed in the closed space. By making such arrangement, it is possible to carry out imaging of other space stably, independent of an environment of the other space. Imaging by a capsule endoscope is an example of such imaging.

In a capsule endoscope, imaging of various parts in body is carried out. For imaging, a subject has to swallow the capsule endoscope. Therefore, in the capsule endoscope, it is necessary to make the image pickup apparatus water-tight, as well as to minimize a resistance at the time of swallowing and a friction with each organ in the body. For this, it is possible to meet these requirements by making both surfaces of the optical member curved surfaces. In such manner, by making the abovementioned arrangement, it is possible to use the image pickup apparatus of the present embodiment as an image pickup apparatus of a capsule endoscope. Moreover, even for applications other than imaging inside the body, it is possible to protect the optical system by the optical member.

In the image pickup apparatus of the present embodiment, it is preferable that the following conditional expression (23) be satisfied:

$$30<|Fc/FL| \quad (23),$$

where,

Fc denotes a focal length of the optical member, and
FL denotes the focal length of the overall optical system.

By satisfying conditional expression (23), it is possible to maintain an imaging performance of the optical system to be favorable even when an accuracy of assembling during manufacturing of the optical system is reduced.

An optical apparatus of the present embodiment includes the abovementioned image pickup apparatus and a signal processing circuit.

According to the optical apparatus of the present embodiment, it is possible to achieve an image having a high resolution and a wide angle of view, while being small-sized.

The image pickup apparatus and the optical apparatus described above may satisfy a plurality of arrangements simultaneously. Making such arrangement is preferable for achieving a favorable image pickup apparatus and optical apparatus. Moreover, combinations of preferable arrangements are arbitrary. Furthermore, regarding each conditional expression, only an upper limit value or a lower limit value of a further restricted numerical range of the conditional expression may be restricted.

Examples of an image pickup apparatus according to certain aspects of the present invention will be described below in detail by referring to the accompanying diagrams. However, the present invention is not restricted to the examples described below. An optical system of the image pickup apparatus will be described below. It is assumed that the image sensor is disposed at an image position formed by the optical system.

In diagrams of the examples, FIG. 1A, FIG. 2A, FIG. 3A, FIG. 4A, FIG. 5A, FIG. 6A, FIG. 7A, FIG. 8A, FIG. 9A, FIG. 10A, FIG. 11A, FIG. 12A, FIG. 13A, FIG. 14A, and FIG. 15A are lens cross-sectional views.

FIG. 1B, FIG. 2B, FIG. 3B, FIG. 4B, FIG. 5B, FIG. 6B, FIG. 7B, FIG. 8B, FIG. 9B, FIG. 10B, FIG. 11B, FIG. 12B, FIG. 13B, FIG. 14B, and FIG. 15B show a spherical aberration (SA).

FIG. 1C, FIG. 2C, FIG. 3C, FIG. 4C, FIG. 5C, FIG. 6C, FIG. 7C, FIG. 8C, FIG. 9C, FIG. 10C, FIG. 11C, FIG. 12C, FIG. 13C, FIG. 14C, and FIG. 15C show an astigmatism (AS).

FIG. 1D, FIG. 2D, FIG. 3D, FIG. 4D, FIG. 5D, FIG. 6D, FIG. 7D, FIG. 8D, FIG. 9D, FIG. 10D, FIG. 11D, FIG. 12D, FIG. 13D, FIG. 14D, and FIG. 15D show a distortion (DT).

FIG. 1E, FIG. 2E, FIG. 3E, FIG. 4E, FIG. 5E, FIG. 6E, FIG. 7E, FIG. 8E, FIG. 9E, FIG. 10E, FIG. 11E, FIG. 12E, FIG. 13E, FIG. 14E, and FIG. 15E show a chromatic aberration (CC) of magnification.

An optical system of an example 1 includes in order from an object side, a negative meniscus lens L1 having a convex surface directed toward the object side, a negative meniscus lens L2 having a convex surface directed toward the object side, a biconvex positive lens L3, and a biconvex positive lens L4.

An aperture stop S is disposed between the biconvex positive lens L3 and the biconvex positive lens L4.

An aspheric surface is provided to a total of six surfaces which are, both surfaces of the negative meniscus lens L2, both surfaces of the biconvex positive lens L3, and both surfaces of the biconvex positive lens L4.

An optical system of an example 2 includes in order from an object side, a negative meniscus lens L1 having a convex surface directed toward the object side, a negative meniscus lens L2 having a convex surface directed toward the object side, a biconvex positive lens L3, and a biconvex positive lens L4.

An aperture stop S is disposed between the biconvex positive lens L3 and the biconvex positive lens L4.

An aspheric surface is provided to a total of six surfaces, which are, both surfaces of the negative meniscus lens L2, both surfaces of the biconvex positive lens L3, and both surfaces of the biconvex positive lens L4.

An optical system of an example 3 includes in order from an object side, a negative meniscus lens L1 having a convex surface directed toward the object side, a negative meniscus lens L2 having a convex surface directed toward the object side, a biconvex positive lens L3, and a biconvex positive lens L4.

An aperture stop S is disposed between the biconvex positive lens L3 and the biconvex positive lens L4.

An aspheric surface is provided to a total of six surfaces which are, both surfaces of the negative meniscus lens L2, both surfaces of the biconvex positive lens L3, and both surfaces of the biconvex positive lens L4.

An optical system of an example 4 includes in order form an object side, a negative meniscus lens L1 having a convex surface directed toward the object side, a biconcave negative lens L2, a biconvex positive lens L3, and a biconvex positive lens L4.

An aperture stop S is disposed between the biconvex positive lens L3 and the biconvex positive lens L4.

An aspheric surface is provided to a total of six surfaces which are, both surfaces of the biconcave negative lens L2, both surfaces of the biconvex positive lens L3, and both surfaces of the biconvex positive lens L4.

An optical system of an example 5 includes in order from an object side, a negative meniscus lens L1 having a convex surface directed toward the object side, a biconcave negative lens L2, a biconvex positive lens L3, and a biconvex positive lens L4.

An aperture stop S is disposed between the biconvex positive lens L3 and the biconvex positive lens L4.

An aspheric surface is provided to a total of six surfaces which are, both surfaces of the biconcave negative lens L2, both surfaces of the biconvex positive lens L3, and both surfaces of the biconvex positive lens L4.

An optical system of an example 6 includes in order from an object side, a negative meniscus lens L1 having a convex surface directed toward the object side, a negative meniscus lens L2 having a convex surface directed toward the object side, a biconvex positive lens L3, and a biconvex positive lens L4.

An aperture stop S is disposed between the biconvex positive lens L3 and the biconvex positive lens L4.

An aspheric surface is provided to a total of six surfaces which are, both surfaces of the negative meniscus lens L2, both surfaces of the biconvex positive lens L3, and both surfaces of the biconvex positive lens L4.

An optical system of an example 7 includes in order from an object side, a negative meniscus lens L1 having a convex surface directed toward the object side, a biconcave negative lens L2, a biconvex positive lens L3, and a positive meniscus lens L4 having a convex surface directed toward an image side.

An aperture stop S is disposed between the biconvex positive lens L3 and the positive meniscus lens L4.

An aspheric surface is provided to a total of seven surfaces which are, an image-side surface of the negative meniscus lens L1, both surfaces of the biconcave negative lens L2, both surfaces of the biconvex positive lens L3, and both surfaces of the positive meniscus lens L4.

An optical system of an example 8 includes in order from an object side, a negative meniscus lens L1 having a convex surface directed toward the object side, a biconcave negative lens L2, a biconvex positive lens L3, and a biconvex positive lens L4.

An aperture stop S is disposed between the biconvex positive lens L3 and the biconvex positive lens L4.

An aspheric surface is provided to a total of seven surfaces which are, an image-side surface of the negative meniscus lens L1, both surfaces of the biconcave negative lens L2, both surfaces of the biconvex positive lens L3, and both surfaces of the biconvex positive lens L4.

An optical system of an example 9 includes in order from an object side, a negative meniscus lens L1 having a convex surface directed toward the object side, a biconcave negative lens L2, a biconvex positive lens L3, and a positive meniscus lens L4 having a convex surface directed toward the object side.

An aperture stop S is disposed between the biconvex positive lens L3 and the positive meniscus lens L4.

An aspheric surface is provided to a total of seven surfaces which are, an image-side surface of the negative meniscus lens L1, both surfaces of the biconcave negative lens L2, both surfaces of the biconvex positive lens L3, and both surfaces of the positive meniscus lens L4.

An optical system of an example 10 includes in order from an object side, a negative meniscus lens L1 having a convex surface directed toward the object side, a negative meniscus lens L2 having a convex surface directed toward an image side, a biconvex positive lens L3, and a biconvex positive lens L4.

An aperture stop S is disposed between the biconvex positive lens L3 and the biconvex positive lens L4.

An aspheric surface is provided to a total of seven surfaces which are, an image-side surface of the negative meniscus lens L1, both surfaces of the negative meniscus lens L2, both surfaces of the biconvex positive lens L3, and both surfaces of the biconvex positive lens L4.

An optical system of an example 11 includes in order from an object side, a negative meniscus lens L1 having a convex surface directed toward the object side, a biconcave negative lens L2, a biconvex positive lens L3, and a biconvex positive lens L4.

An aperture stop S is disposed between the biconvex positive lens L3 and the biconvex positive lens L4.

An aspheric surface is provided to a total of six surfaces which are both surfaces of the biconcave negative lens L2, both surfaces of the biconvex positive lens L3, and both surfaces of the biconvex positive lens L4.

An optical system of an example 12 includes in order from an object side, a negative meniscus lens L1 having a convex surface directed toward the object side, a biconcave negative lens L2, a biconvex positive lens L3, and a positive meniscus lens L4 having a convex surface directed toward the object side.

An aperture stop S is disposed between the biconvex positive lens L3 and the positive meniscus lens L4.

An aspheric surface is provided to a total of six surfaces which are, both surfaces of the biconcave negative lens L2, both surfaces of the biconvex positive lens L3, and both surfaces of the positive meniscus lens L4.

An optical system of an example 13 includes in order from an object side, a negative meniscus lens L1 having a convex surface directed toward the object side, a biconcave negative lens L2, a biconvex positive lens L3, and a biconvex positive lens L4.

An aperture stop S is disposed between the biconvex positive lens L3 and the biconvex positive lens L4.

An aspheric surface is provided to a total of seven surfaces which are, an image-side surface of the negative meniscus lens L1, both surfaces of the biconcave negative lens L2, both surfaces of the biconvex positive lens L3, and both surfaces of the biconvex positive lens L4.

An optical system of an example 14 includes in order from an object side, a negative meniscus lens L1 having a convex surface directed toward the object side, a biconcave negative lens L2, a biconvex positive lens L3, and a positive meniscus lens L4 having a convex surface directed toward the object side.

An aperture stop S is disposed between the biconvex positive lens L3 and the positive meniscus lens L4.

An aspheric surface is provided to a total of six surfaces which are, both surfaces of the biconcave negative lens L2, both surfaces of the biconvex positive lens L3, and both surfaces of the positive meniscus lens L4.

An optical system of an example 15 includes in order from an object side, a negative meniscus lens L1 having a convex surface directed toward the object side, a biconcave negative lens L2, a biconvex positive lens L3, and a positive meniscus lens L4 having a convex surface directed toward the object side.

An aperture stop S is disposed between the biconvex positive lens L3 and the positive meniscus lens L4.

An aspheric surface is provided to a total of six surfaces which are, both surfaces of the biconcave negative lens L2, both surfaces of the biconvex positive lens L3, and both surfaces of the positive meniscus lens L4.

A wide-angle optical system according to an example 16, as shown in FIG. 16, includes in order from an object side, an optical member CG, a negative meniscus lens L1 having a convex surface directed toward the object side, a biconcave negative lens L2, a biconvex positive lens L3, and a biconvex positive lens L4. The optical system including the negative meniscus lens L1, the biconcave negative lens L2, the biconvex positive lens L3, an aperture stop S, and the biconvex positive lens L4 is same as the optical system according to the example 5.

FIG. 16 is a schematic diagram illustrating that the optical member CG can be disposed. Therefore, a size and a position of the optical member CG have not been depicted accurately with respect to sizes and positions of the lenses.

The optical member CG is a member in the form of a plate, and both an object-side surface and an image-side surface thereof are curved surfaces. In FIG. 16, since both the object-side surface and the image-side surface are curved surfaces, an overall shape of the optical member CG is hemispherical. In the example 16, a thickness of the optical member CG, or in other words, a distance between the object-side surface and the image-side surface, is constant. However, the thickness of the optical member CG may not be constant.

Moreover, as it will be described later, the optical member CG is disposed at a position only 4.75 mm away on the object side from the object-side surface of the first lens. However, the optical member CG may be disposed at a position shifted frontward or rearward from the abovementioned position. Moreover, a radius of curvature and the thickness of the optical member CG mentioned here is an example, and are not limited to the radius of curvature and the thickness mentioned here.

A material that allows light to transmit through has been used for the optical member CG. Consequently, light from an object passes through the optical member CG and is incident on the negative meniscus lens L1. The optical member CG is disposed such that a curvature center of the image-side surface substantially coincides with a position of an entrance pupil. Consequently, a new aberration due to the optical member CG hardly occurs. In other words, an imaging performance of the optical system according to the example 16 is not different from an imaging performance of the optical system according to the example 5.

The optical member CG functions as a cover glass. In this case, the optical member CG corresponds to an observation window provided at an outer covering of a capsule endoscope. Therefore, the optical system according to the example 16 can be used for an optical system of a capsule endoscope. The optical systems according to the example 1 to the example 4, and example 6 to the example 15 can also be used for an optical system of an endoscope.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens and *denotes an aspheric surface, stop denotes an aperture stop.

In surface data of each example, a flat surface is positioned immediately next to a surface indicating a stop. This flat surface indicates an image-side surface of the stop. For example, in the example 1, a seventh surface (r7) is an object-side surface of a stop, and an eighth surface (r8) is an image-side surface of the stop. Therefore, a distance (d7)

between the seventh surface and the eighth surface becomes a thickness of the stop. Similar is the case even for the other examples.

Further, in Various data, f denotes a focal length of the entire system, FNO. denotes an F number, ω denotes a half angle of view, IH denotes an image height, LTL denotes a lens total length of the optical system, BF denotes aback focus. Further, back focus is a unit which is expressed upon air conversion of a distance from a rearmost lens surface to a paraxial image surface. The lens total length is a distance from a frontmost lens surface to the rearmost lens surface plus back focus. A unit of the half angle of view is degree.

Moreover, the example 16 is an example in which the optical member CG is disposed on the object side of the image forming optical system according to the example 5. In surface data of the example 16, C1 denotes the object-side surface of the optical member CG and C2 denotes the image-side surface of the optical member CG. Since aspheric surface data and various data of the example 16 are same as aspheric surface data and various data of the example 5, description thereof is omitted here.

A shape of an aspheric surface is defined by the following expression where the direction of the optical axis is represented by z, the direction orthogonal to the optical axis is represented by y, a conical coefficient is represented by K, aspheric surface coefficients are represented by A4, A6, A8, A10, A12 . . . .

$$Z=(y^2/r)/[1+\{1-(1+k)(y/r)^2\}^{1/2}]+A4\,y^4+A6\,y^6+A8\,y^8+A10\,y^{10}+A12\,y^{12}+\ldots$$

Further, in the aspheric surface coefficients, 'e-n' (where, n is an integral number) indicates '$10^{-n}$'. Moreover, these symbols are commonly used in the following numerical data for each example.

Example 1

| Unit mm | | | | |
|---|---|---|---|---|
| Surface data | | | | |
| Surface no. | r | d | nd | vd |
| Object plane | 11.335 | 10.20 | | |
| 1 | 7.934 | 0.34 | 1.53110 | 56.00 |
| 2 | 1.893 | 0.58 | | |
| 3* | 5.667 | 0.34 | 1.53110 | 56.00 |
| 4* | 0.972 | 0.45 | | |
| 5* | 1.140 | 0.67 | 1.63493 | 23.89 |
| 6* | −2.107 | 0.03 | | |
| 7(Stop) | ∞ | 0.06 | | |
| 8 | ∞ | 0.35 | | |
| 9* | 1.357 | 1.04 | 1.53110 | 56.00 |
| 10* | −12.095 | 0.61 | | |
| Image plane | ∞ | | | |

Aspheric surface data

3rd surface k = 0.000
A4 = −4.80693e−02
4th surface k = 0.000
A4 = 4.96932e−01, A6 = −1.71709e−01, A8 = −3.35785e−01
5th surface k = −1.163
A4 = 4.49400e−02, A6 = −5.07912e−01

-continued

| Unit mm |
|---|
| 6th surface | k = 0.000
A4 = −1.14989e−01, A6 = −5.18067e−03
9th surface k = 0.000
A4 = −4.12388e−01, A6 = 2.57924e−01
10th surface k = 0.000
A4 = −1.72443e−01

| Various data | |
|---|---|
| f | 1.00 |
| FNO. | 3.50 |
| 2ω | 184.7 |
| IH | 1.11 |
| LTL | 4.47 |
| BF | 0.61 |
| Φ1L | 2.06 |

Example 2

| Unit mm | | | | |
|---|---|---|---|---|
| Surface data | | | | |
| Surface no. | r | d | nd | vd |
| Object plane | 11.644 | 10.48 | | |
| 1 | 8.151 | 0.35 | 1.53110 | 56.00 |
| 2 | 1.812 | 0.65 | | |
| 3* | 5.822 | 0.35 | 1.53110 | 56.00 |
| 4* | 0.999 | 0.45 | | |
| 5* | 1.526 | 0.65 | 1.65100 | 21.50 |
| 6* | −1.563 | 0.03 | | |
| 7(Stop) | ∞ | 0.06 | | |
| 8 | ∞ | 0.49 | | |
| 9* | 1.482 | 0.96 | 1.53110 | 56.00 |
| 10* | −11.735 | 0.70 | | |
| Image plane | ∞ | | | |

Aspheric surface data

3rd surface k = 0.000
A4 = −5.68331e−02, A6 = −5.27884e−03, A8 = −9.97307e−03
4th surface k = 0.000
A4 = 4.38554e−01, A6 = −8.69895e−02, A8 = −2.74029e−01
5th surface k = −0.740
A4 = 1.03933e−01, A6 = −5.36026e−01, A8 = −2.09610e−01
6th surface k = 0.000
A4 = −3.83834e−02, A6 = 1.76425e−01, A8 = 3.34578e−02
9th surface k = 0.000
A4 = −3.46551e−01, A6 = 1.86562e−01, A8 = −5.05644e−02
10th surface k = 0.000
A4 = −9.87669e−02, A6 = −7.33529e−03, A8 = −1.11324e−02

-continued

Unit mm

Various data

| | |
|---|---|
| f | 1.00 |
| FNO. | 3.00 |
| 2ω | 177.4 |
| IH | 1.14 |
| LTL | 4.69 |
| BF | 0.70 |
| Φ1L | 2.04 |

Example 3

Unit mm

Surface data

| Surface no. | r | d | nd | vd |
|---|---|---|---|---|
| Object plane | 11.575 | 10.42 | | |
| 1 | 5.788 | 0.35 | 1.53110 | 56.00 |
| 2 | 1.285 | 0.62 | | |
| 3* | 5.788 | 0.35 | 1.53110 | 56.00 |
| 4* | 0.933 | 0.38 | | |
| 5* | 1.082 | 0.72 | 1.63493 | 23.89 |
| 6* | −1.653 | 0.03 | | |
| 7(Stop) | ∞ | 0.06 | | |
| 8 | ∞ | 0.32 | | |
| 9* | 1.925 | 1.13 | 1.53110 | 56.00 |
| 10* | −12.351 | 0.67 | | |
| Image plane | ∞ | | | |

Aspheric surface data

3rd surface k = 0.000
A4 = 3.69493e-03, A6 = −5.88456e-02, A8 = −4.41568e-04

4th surface k = 0.000
A4 = 5.36955e-01, A6 = −9.14916e-02, A8 = −1.94782e-01

5th surface k = −0.920
A4 = −3.39676e-02, A6 = −4.34433e-01, A8 = −2.89742e-02

6th surface k = 0.000
A4 = −2.25321e-01, A6 = 1.13117e-01, A8 = 3.00186e-02

9th surface k = 0.000
A4 = −4.15021e-01, A6 = 4.32835e-01, A8 = −1.70600e-02

10th surface k = 0.000
A4 = −2.38707e-01, A6 = −3.75300e-03, A8 = −3.92398e-03

Various data

| | |
|---|---|
| f | 1.00 |
| FNO. | 3.50 |
| 2ω | 186.9 |
| IH | 1.13 |
| LTL | 4.63 |
| BF | 0.67 |
| Φ1L | 2.02 |

Example 4

Unit mm

Surface data

| Surface no. | r | d | nd | vd |
|---|---|---|---|---|
| Object plane | ∞ | 13.63 | | |
| 1 | 10.992 | 0.33 | 1.58500 | 30.00 |
| 2 | 1.330 | 0.82 | | |
| 3* | −3.321 | 0.33 | 1.53110 | 56.00 |
| 4* | 0.824 | 0.21 | | |
| 5* | 0.599 | 0.89 | 1.58500 | 30.00 |
| 6* | −1.549 | 0.03 | | |
| 7(Stop) | ∞ | 0.06 | | |
| 8 | ∞ | 0.58 | | |
| 9* | 3.335 | 0.89 | 1.53110 | 56.00 |
| 10* | −18.201 | 0.59 | | |
| Image plane | ∞ | | | |

Aspheric surface data

3rd surface k = 0.000
A4 = −4.60810e-02, A6 = −2.53692e-02, A8 = 3.94763e-06

4th surface k = 0.000
A4 = −2.34423e-01, A6 = −2.14933e-01, A8 = −1.76040e-01

5th surface k = −1.254
A4 = 1.15646e-01, A6 = −8.99601e-02, A8 = 3.25666e-03

6th surface k = 0.000
A4 = 4.02575e-01, A6 = 6.68567e-03, A8 = 3.29862e-04

9th surface k = 0.000
A4 = −1.96156e-01, A6 = −1.65306e-02, A8 = −4.29908e-03

10th surface k = 0.000
A4 = −1.29378e-01, A6 = −8.99012e-02, A8 = −7.90286e-04

Various data

| | |
|---|---|
| f | 1.00 |
| FNO. | 4.00 |
| 2ω | 170.7 |
| IH | 1.09 |
| LTL | 4.73 |
| BF | 0.59 |
| Φ1L | 1.72 |

Example 5

Unit mm

Surface data

| Surface no. | r | d | nd | vd |
|---|---|---|---|---|
| Object plane | ∞ | 14.36 | | |
| 1 | 9.266 | 0.35 | 1.53110 | 56.00 |
| 2 | 1.302 | 0.89 | | |
| 3* | −5.850 | 0.35 | 1.53110 | 56.00 |
| 4* | 0.835 | 0.24 | | |
| 5* | 0.733 | 0.81 | 1.58500 | 30.00 |
| 6* | −1.500 | 0.03 | | |
| 7(Stop) | ∞ | 0.06 | | |

-continued

| Unit mm | | | | |
|---|---|---|---|---|
| 8 | ∞ | 0.61 | | |
| 9* | 2.209 | 0.95 | 1.53110 | 56.00 |
| 10* | −15.578 | 0.68 | | |
| Image plane | ∞ | | | |

Aspheric surface data

3rd surface k = 0.000
A4 = −5.91753e−02, A6 = −3.29380e−02, A8 = 1.08336e−03
4th surface k = 0.000
A4 = −2.56359e−01, A6 = −1.89685e−01, A8 = −9.64225e−02
5th surface k = −1.751
A4 = 2.94042e−02, A6 = −1.17809e−02, A8 = 3.00680e−02
6th surface k = 0.000
A4 = 1.33106e−01, A6 = −5.35349e−02, A8 = 5.21750e−03
9th surface k = 0.000
A4 = −2.09685e−01, A6 = 3.58779e−02, A8 = −2.39322e−03
10th surface k = 0.000
A4 = −3.14701e−02, A6 = −1.06856e−01, A8 = −2.11857e−03

Various data

| f | 1.00 |
|---|---|
| FNO. | 4.50 |
| 2ω | 174.4 |
| IH | 1.14 |
| LTL | 4.97 |
| BF | 0.68 |
| Φ1L | 1.93 |

Example 6

| Unit mm | | | | |
|---|---|---|---|---|
| Surface data | | | | |
| Surface no. | r | d | nd | vd |
| Object plane | ∞ | 14.11 | | |
| 1 | 34.130 | 0.34 | 1.53110 | 56.00 |
| 2 | 1.355 | 0.84 | | |
| 3* | 8.564 | 0.34 | 1.53110 | 56.00 |
| 4* | 0.805 | 0.30 | | |
| 5* | 0.970 | 0.71 | 1.58500 | 30.00 |
| 6* | −1.246 | 0.03 | | |
| 7(Stop) | ∞ | 0.06 | | |
| 8 | ∞ | 0.63 | | |
| 9* | 2.434 | 0.90 | 1.53110 | 56.00 |
| 10* | −16.677 | 0.79 | | |
| Image plane | ∞ | | | |

Aspheric surface data

3rd surface k = 0.000
A4 = −8.43833e−02, A6 = −1.05006e−01, A8 = −2.67160e−03
4th surface k = 0.000
A4 = −3.15336e−01, A6 = −1.10611e−01, A8 = −2.38690e−02

5th surface k = −2.059
A4 = −1.10973e−01, A6 = −2.07461e−01, A8 = −6.79230e−03
6th surface k = 0.000
A4 = −1.47047e−02, A6 = −3.86310e−02, A8 = 1.42218e−04
9th surface k = 0.000
A4 = −3.43961e−01, A6 = 8.65281e−03, A8 = −3.03525e−03
10th surface k = 0.000
A4 = −1.56693e−02, A6 = −1.82646e−01, A8 = −3.20979e−05

Various data

| f | 1.00 |
|---|---|
| FNO. | 4.50 |
| 2ω | 165.4 |
| IH | 1.11 |
| LTL | 4.94 |
| BF | 0.79 |
| Φ1L | 1.71 |

Example 7

| Unit mm | | | | |
|---|---|---|---|---|
| Surface data | | | | |
| Surface no. | r | d | nd | vd |
| Object plane | ∞ | 13.14 | | |
| 1 | 52.985 | 0.32 | 1.53110 | 56.00 |
| 2* | 1.138 | 0.82 | | |
| 3* | −1.980 | 0.32 | 1.53110 | 56.00 |
| 4* | 19.766 | 0.18 | | |
| 5* | 1.134 | 0.61 | 1.58500 | 30.00 |
| 6* | −1.061 | 0.03 | | |
| 7(Stop) | ∞ | 0.06 | | |
| 8 | ∞ | 0.43 | | |
| 9* | −52.985 | 1.07 | 1.53110 | 56.00 |
| 10* | −4.308 | 0.63 | | |
| Image plane | ∞ | | | |

Aspheric surface data

2nd surface k = 0.000
A4 = 1.35896e−02, A6 = 6.33910e−03, A8 = 6.87352e−04
3rd surface k = 0.000
A4 = −1.39300e−02, A6 = 6.16347e−04, A8 = 4.58306e−02
4th surface k = 0.000
A4 = −1.14268e−01, A6 = 8.39589e−01, A8 = −8.67101e−02
5th surface k = 0.000
A4 = −6.55723e−01, A6 = −8.03651e−02, A8 = 3.60648e−01
6th surface k = 0.000
A4 = −3.74570e−01, A6 = 2.31365e−01, A8 = 2.64260e+01

-continued

| Unit mm | | |
|---|---|---|
| 9th surface | | | k = 0.000
A4 = −7.51808e−01, A6 = 1.44317e−01, A8 = 2.64449e−01
10th surface k = 0.000
A4 = 6.22249e−02, A6 = −5.25246e−01, A8 = 1.67696e−01

| Various data | |
|---|---|
| f | 1.00 |
| FNO. | 4.00 |
| 2ω | 166.4 |
| IH | 1.03 |
| LTL | 4.46 |
| BF | 0.63 |
| Φ1L | 1.48 |

Example 8

| Unit mm | | | | |
|---|---|---|---|---|
| Surface data | | | | |
| Surface no. | r | d | nd | vd |
| Object plane | ∞ | 13.94 | | |
| 1 | 56.192 | 0.34 | 1.53110 | 56.00 |
| 2* | 1.346 | 0.97 | | |
| 3* | −2.640 | 0.34 | 1.53110 | 56.00 |
| 4* | 3.813 | 0.21 | | |
| 5* | 1.138 | 0.70 | 1.58500 | 30.00 |
| 6* | −1.575 | 0.03 | | |
| 7(Stop) | ∞ | 0.06 | | |
| 8 | ∞ | 0.57 | | |
| 9* | 2.023 | 0.94 | 1.53110 | 56.00 |
| 10* | −10.817 | 0.75 | | |
| Image plane | ∞ | | | |

Aspheric surface data

2nd surface k = 0.000
A4 = 9.70889e−04, A6 = 6.08358e−04
3rd surface k = −15.846
A4 = 3.80865e−04, A6 = 6.33172e−04
4th surface k = 30.000
A4 = −1.50561e−01, A6 = 2.78890e−01
5th surface k = 0.000
A4 = −4.44141e−01, A6 = 3.85497e−03
6th surface k = 0.000
A4 = −1.62573e−01, A6 = 3.34516e−02
9th surface k = 0.000
A4 = −2.51080e−01, A6 = −3.83712e−01
10th surface k = 0.000
A4 = 1.35192e−01, A6 = −4.12607e−01, A8 = 7.22857e−02

-continued

| Unit mm | |
|---|---|
| Various data | |
| f | 1.00 |
| FNO. | 2.80 |
| 2ω | 165.5 |
| IH | 1.10 |
| LTL | 4.90 |
| BF | 0.75 |
| Φ1L | 1.79 |

Example 9

| Unit mm | | | | |
|---|---|---|---|---|
| Surface data | | | | |
| Surface no. | r | d | nd | vd |
| Object plane | ∞ | 14.05 | | |
| 1 | 113.344 | 0.34 | 1.53110 | 56.00 |
| 2* | 1.334 | 0.98 | | |
| 3* | −3.496 | 0.34 | 1.53110 | 56.00 |
| 4* | 3.599 | 0.19 | | |
| 5* | 1.130 | 0.73 | 1.58500 | 30.00 |
| 6* | −1.550 | 0.03 | | |
| 7(Stop) | ∞ | 0.06 | | |
| 8 | ∞ | 0.46 | | |
| 9* | 2.040 | 0.95 | 1.53110 | 56.00 |
| 10* | 219.950 | 0.73 | | |
| Image plane | ∞ | | | |

Aspheric surface data

2nd surface k = 0.000
3rd surface k = −23.102
4th surface k = 30.000
A4 = −1.56920e−01, A6 = 2.67286e−01
5th surface k = 0.000
A4 = −4.22868e−01
6th surface k = 0.000
A4 = −1.30330e−01, A6 = 3.96216e−02
9th surface k = 0.000
A4 = −2.64274e−01, A6 = −3.90853e−01
10th surface k = 0.000
A4 = 1.46960e−01, A6 = −3.92625e−01, A8 = 6.59913e−02

| Various data | |
|---|---|
| f | 1.00 |
| FNO. | 2.80 |
| 2ω | 165.5 |
| IH | 1.10 |
| LTL | 4.81 |
| BF | 0.73 |
| Φ1L | 1.78 |

Example 10

Unit mm

Surface data

| Surface no. | r | d | nd | vd |
|---|---|---|---|---|
| Object plane | ∞ | 14.36 | | |
| 1 | 115.812 | 0.35 | 1.53110 | 56.00 |
| 2* | 1.324 | 1.04 | | |
| 3* | −2.011 | 0.35 | 1.53110 | 56.00 |
| 4* | −16.010 | 0.22 | | |
| 5* | 1.095 | 0.69 | 1.58500 | 30.00 |
| 6* | −2.184 | 0.03 | | |
| 7(Stop) | ∞ | 0.06 | | |
| 8 | ∞ | 0.42 | | |
| 9* | 2.085 | 0.97 | 1.53110 | 56.00 |
| 10* | −50.646 | 0.74 | | |
| Image plane | ∞ | | | |

Aspheric surface data

2nd surface k = 0.000
A4 = −1.30262e−02, A6 = −5.67154e−03, A8 = −8.46271e−04

3rd surface k = −11.257
A4 = 3.98509e−03, A6 = −7.08884e−03, A8 = −4.49387e−02

4th surface k = 0.000
A4 = 5.33704e−02, A6 = 6.02235e−02, A8 = 2.67858e−02

5th surface k = 0.000
A4 = −3.42506e−01, A6 = −8.29827e−02, A8 = −2.87050e−02

6th surface k = 0.000
A4 = −1.75043e−01, A6 = −2.00184e−02, A8 = −4.57555e−05

9th surface k = 0.000
A4 = −4.12047e−01, A6 = −1.54248e−01, A8 = −4.95521e−02

10th surface k = 0.000
A4 = 9.85228e−02, A6 = −3.21853e−01, A8 = 2.57604e−02

Various data

| | |
|---|---|
| f | 1.00 |
| FNO. | 3.70 |
| 2ω | 165.5 |
| IH | 1.12 |
| LTL | 4.89 |
| BF | 0.74 |
| Φ1L | 1.79 |

Example 11

Unit mm

Surface data

| Surface no. | r | d | nd | vd |
|---|---|---|---|---|
| Object plane | ∞ | 14.30 | | |
| 1 | 10.167 | 0.35 | 1.53110 | 56.00 |
| 2 | 1.555 | 0.99 | | |
| 3* | −6.566 | 0.35 | 1.53110 | 56.00 |
| 4* | 1.800 | 0.44 | | |
| 5* | 1.238 | 0.71 | 1.58500 | 30.00 |
| 6* | −1.087 | 0.03 | | |
| 7(Stop) | ∞ | 0.06 | | |
| 8 | ∞ | 0.49 | | |
| 9* | 17.298 | 0.86 | 1.53110 | 56.00 |
| 10* | −10.313 | 0.67 | | |
| Image plane | ∞ | | | |

Aspheric surface data

3rd surface k = 0.000
A4 = −3.26049e−02, A6 = −1.73396e−04, A8 = −1.79759e−03

4th surface k = 0.000
A4 = −5.56346e−02, A6 = 4.39405e−01, A8 = −6.29700e−02

5th surface k = 0.000
A4 = −4.47881e−01, A6 = −7.40999e−02, A8 = −7.23506e−02

6th surface k = 0.000
A4 = −6.69872e−02, A6 = −6.50344e−02, A8 = −1.07138e−02

9th surface k = 0.000
A4 = −3.76689e−01, A6 = −3.75298e−01, A8 = −1.82810e−01

10th surface k = 0.000
A4 = 5.36738e−02, A6 = −3.77720e−01, A8 = 7.09463e−02

Various data

| | |
|---|---|
| f | 1.00 |
| FNO. | 3.70 |
| 2ω | 165.4 |
| IH | 1.13 |
| LTL | 4.95 |
| BF | 0.67 |
| Φ1L | 2.09 |

Example 12

Unit mm

Surface data

| Surface no. | r | d | nd | vd |
|---|---|---|---|---|
| Object plane | ∞ | 14.43 | | |
| 1 | 9.630 | 0.35 | 1.53110 | 56.00 |
| 2 | 1.461 | 0.97 | | |
| 3* | −4.199 | 0.35 | 1.53110 | 56.00 |
| 4* | 2.874 | 0.27 | | |
| 5* | 1.429 | 0.68 | 1.58500 | 30.00 |
| 6* | −1.053 | 0.03 | | |
| 7(Stop) | ∞ | 0.06 | | |
| 8 | ∞ | 0.52 | | |
| 9* | 2.493 | 0.77 | 1.53110 | 56.00 |
| 10* | 5.195 | 0.64 | | |
| Image plane | ∞ | | | |

Aspheric surface data

3rd surface k = 0.000
A4 = −3.11948e−02, A6 = −2.52078e−04, A8 = −1.35304e−03

-continued

| Unit mm |
|---|

4th surface k = 0.000
A4 = 7.37690e−02, A6 = 4.51549e−01, A8 = 6.87041e−02
5th surface k = 0.000
A4 = −4.24390e−01
6th surface k = 0.000
A4 = −5.37916e−02, A6 = −2.29133e−02, A8 = 7.82891e−04
9th surface k = 0.000
A4 = −2.31127e−01, A6 = −6.23266e−02, A8 = −5.27980e−02
10th surface k = 0.000
A4 = 7.24503e−02, A6 = −2.88971e−01, A8 = 6.82544e−02

| Various data | |
|---|---|
| f | 1.00 |
| FNO. | 3.70 |
| 2ω | 165.4 |
| IH | 1.13 |
| LTL | 4.65 |
| BF | 0.64 |
| Φ1L | 1.99 |

Example 13

| Unit mm | | | |
|---|---|---|---|
| Surface data | | | |
| Surface no. | r | d | nd | vd |
| Object plane | ∞ | 14.35 | | |
| 1 | 13.105 | 0.34 | 1.53110 | 56.00 |
| 2* | 1.743 | 1.01 | | |
| 3* | −8.456 | 0.34 | 1.53110 | 56.00 |
| 4* | 1.051 | 0.32 | | |
| 5* | 1.349 | 0.99 | 1.58500 | 30.00 |
| 6* | −1.214 | 0.06 | | |
| 7(Stop) | ∞ | 0.06 | | |
| 8 | ∞ | 0.70 | | |
| 9* | 1.909 | 0.63 | 1.53110 | 56.00 |
| 10* | −16.821 | 1.02 | | |
| Image plane | ∞ | | | |

| Aspheric surface data |
|---|

2nd surface k = 0.000
A4 = −3.60965e−02, A6 = 8.42392e−03
3rd surface k = 0.000
A4 = 9.08146e−02, A6 = −9.01046e−02
4th surface k = 0.000
A4 = 2.45973e−01, A6 = 1.06391e−02
5th surface k = 0.000
A4 = −2.20568e−01, A6 = −7.39078e−02

-continued

| Unit mm |
|---|

6th surface k = 0.000
A4 = −2.26284e−02
9th surface k = 0.000
A4 = −2.00902e−01, A6 = −6.10429e−02
10th surface k = 0.000
A4 = −8.19537e−03, A6 = −1.96347e−01

| Various data | |
|---|---|
| f | 1.00 |
| FNO. | 3.50 |
| 2ω | 165.1 |
| IH | 1.11 |
| LTL | 5.48 |
| BF | 1.02 |
| Φ1L | 2.19 |

Example 14

| Unit mm | | | |
|---|---|---|---|
| Surface data | | | |
| Surface no. | r | d | nd | vd |
| Object plane | ∞ | 14.52 | | |
| 1 | 8.115 | 0.35 | 1.53110 | 56.00 |
| 2 | 1.284 | 0.83 | | |
| 3* | −6.990 | 0.35 | 1.53110 | 56.00 |
| 4* | 0.761 | 0.13 | | |
| 5* | 0.796 | 0.58 | 1.58500 | 30.00 |
| 6* | −1.084 | 0.03 | | |
| 7(Stop) | ∞ | 0.06 | | |
| 8 | ∞ | 0.69 | | |
| 9* | 1.600 | 0.67 | 1.53110 | 56.00 |
| 10* | 26.283 | 0.76 | | |
| Image plane | ∞ | | | |

| Aspheric surface data |
|---|

3rd surface k = 0.000
A4 = −1.43376e−01, A6 = −5.80962e−02, A8 = −1.71168e−04
4th surface k = 0.000
A4 = 2.81041e−01, A6 = −2.49472e−02, A8 = 6.07988e−03
5th surface k = 0.000
A4 = −1.74806e−01, A6 = −2.07877e−02, A8 = −3.00909e−03
6th surface k = 0.000
A4 = 1.41013e−01, A6 = 4.86899e−03, A8 = −2.48119e−03
9th surface k = 0.000
A4 = −2.32522e−01, A6 = 2.90456e−03, A8 = −8.06557e−05
10th surface k = 0.000
A4 = −4.34499e−03, A6 = −1.62862e−01, A8 = 2.32962e−02

Example 15 (continued)

Unit mm

Various data

| | |
|---|---|
| f | 1.00 |
| FNO. | 4.50 |
| 2ω | 165.2 |
| IH | 1.14 |
| LTL | 4.46 |
| BF | 0.76 |
| Φ1L | 1.76 |

Example 15

Unit mm

Surface data

| Surface no. | r | d | nd | vd |
|---|---|---|---|---|
| Object plane | ∞ | 14.93 | | |
| 1 | 7.391 | 0.36 | 1.53110 | 56.00 |
| 2 | 1.911 | 0.62 | | |
| 3* | −12.079 | 0.36 | 1.53110 | 56.00 |
| 4* | 0.844 | 0.51 | | |
| 5* | 1.247 | 0.79 | 1.58500 | 30.00 |
| 6* | −1.315 | 0.08 | | |
| 7(Stop) | ∞ | 0.07 | | |
| 8 | ∞ | 0.87 | | |
| 9* | 1.490 | 0.66 | 1.53110 | 56.00 |
| 10* | 122.982 | 0.82 | | |
| Image plane | ∞ | | | |

Aspheric surface data

3rd surface k = 0.000
A4 = 9.15543e−03, A6 = −2.34000e−02

4th surface k = 0.000
A4 = 7.67666e−02, A6 = 9.41321e−02

5th surface k = 0.000
A4 = −1.41419e−01, A6 = −6.47956e−02

6th surface k = 0.000
A4 = 3.23780e−02, A6 = −2.58691e−03

9th surface k = 0.000
A4 = −8.18973e−02, A6 = −1.90235e−02

10th surface k = 0.000
A4 = 1.30590e−01, A6 = −9.69664e−02

Various data

| | |
|---|---|
| f | 1.00 |
| FNO. | 3.50 |
| 2ω | 165.3 |
| IH | 1.19 |
| LTL | 5.14 |
| BF | 0.82 |
| Φ1L | 1.92 |

Example 16

Unit mm

Surface data

| Surface no. | r | d | nd | vd |
|---|---|---|---|---|
| Object plane | ∞ | 8.22 | | |
| C1 | 6.371 | 1.39 | 1.58500 | 30.00 |
| C2 | 4.981 | 4.75 | | |
| 1 | 9.266 | 0.35 | 1.53110 | 56.00 |
| 2 | 1.302 | 0.89 | | |
| 3* | −5.850 | 0.35 | 1.53110 | 56.00 |
| 4* | 0.835 | 0.24 | | |
| 5* | 0.733 | 0.81 | 1.58500 | 30.00 |
| 6* | −1.500 | 0.03 | | |
| 7(Stop) | ∞ | 0.06 | | |
| 8 | ∞ | 0.61 | | |
| 9* | 2.209 | 0.95 | 1.53110 | 56.00 |
| 10* | −15.578 | 0.68 | | |
| Image plane | ∞ | | | |

Various data

| | |
|---|---|
| fc | −61.85 |

Next, values for conditional expressions in each example will be shown. Since an optical member CG has not been disposed in the optical systems of examples 1 to 15, values for conditional expression (23) are mentioned only in the example 16. The optical member CG in the example 16 may be used in the optical systems of examples 1 to 15.

| | Example1 | Example2 | Example3 | Example4 |
|---|---|---|---|---|
| (1)αmax − αmin | 6.6E−06 | 7.6E−06 | 6.6E−06 | 5.6E−06 |
| (2)R1R/FL | 1.89 | 1.81 | 1.28 | 1.34 |
| (3)D1Ls/DsF | 1.72 | 1.72 | 1.69 | 1.78 |
| (4)FL/R1L | 0.13 | 0.12 | 0.17 | 0.09 |
| (5)R2R/FL | 0.97 | 1.00 | 0.93 | 0.83 |
| (6)FL/R2L | 0.18 | 0.17 | 0.17 | −0.30 |
| (7)Φ1L/IH | 1.87 | 1.79 | 1.80 | 1.60 |
| (8)D1R2L/Σd | 0.15 | 0.16 | 0.16 | 0.20 |
| (9)D2R3L/Σd | 0.12 | 0.11 | 0.10 | 0.05 |
| (10)D3R4L/Σd | 0.12 | 0.15 | 0.11 | 0.16 |
| (11)f1/FL | −4.77 | −4.47 | −3.20 | −2.64 |
| (12)f2/FL | −2.27 | −2.33 | −2.15 | −1.22 |
| (13)f3/FL | 1.27 | 1.29 | 1.15 | 0.88 |
| (14)Σd/FL | 3.86 | 3.99 | 3.96 | 4.17 |
| (15)vd1/vd3 | 2.3 | 2.6 | 2.3 | 1.0 |
| (16)vd2/vd3 | 2.3 | 2.6 | 2.3 | 1.9 |
| (17)vd3/vd4 | 0.4 | 0.4 | 0.4 | 0.5 |
| (18)f1/R1L | −0.602 | −0.549 | −0.552 | −0.238 |
| (19)f2/R2L | −0.4 | −0.4 | −0.4 | 0.4 |
| (20)(R3L + R3R)/(R3L − R3R) | −0.30 | −0.01 | −0.21 | −0.44 |
| (21)Σd/Dmaxair | 6.68 | 6.10 | 6.41 | 5.02 |
| (22)D1Ls/FL | 2.40 | 2.48 | 2.45 | 2.63 |

| | Example5 | Example6 | Example7 | Example8 |
|---|---|---|---|---|
| (1)αmax − αmin | 5.6E−06 | 5.6E−06 | 5.6E−06 | 5.6E−06 |
| (2)R1R/FL | 1.30 | 1.37 | 1.15 | 1.36 |
| (3)D1Ls/DsF | 1.71 | 1.67 | 1.52 | 1.71 |
| (4)FL/R1L | 0.11 | 0.03 | 0.02 | 0.02 |
| (5)R2R/FL | 0.84 | 0.81 | 19.90 | 3.85 |
| (6)FL/R2L | −0.17 | 0.12 | −0.50 | −0.38 |
| (7)Φ1L/IH | 1.71 | 1.55 | 1.44 | 1.63 |
| (8)D1R2L/Σd | 0.21 | 0.20 | 0.21 | 0.23 |
| (9)D2R3L/Σd | 0.06 | 0.07 | 0.05 | 0.05 |
| (10)D3R4L/Σd | 0.17 | 0.18 | 0.13 | 0.16 |

-continued

|  | Example 5 | Example 6 | Example 7 | Example 8 |
|---|---|---|---|---|
| (11)f1/FL | −2.90 | −2.69 | −2.21 | −2.63 |
| (12)f2/FL | −1.35 | −1.72 | −3.40 | −2.91 |
| (13)f3/FL | 0.97 | 1.07 | 1.05 | 1.26 |
| (14)Σd/FL | 4.29 | 4.19 | 3.86 | 4.19 |
| (15)vd1/vd3 | 1.9 | 1.9 | 1.9 | 1.9 |
| (16)vd2/vd3 | 1.9 | 1.9 | 1.9 | 1.9 |
| (17)vd3/vd4 | 0.5 | 0.5 | 0.5 | 0.5 |
| (18)f1/R1L | −0.313 | −0.078 | −0.041 | −0.046 |
| (19)f2/R2L | 0.2 | −0.2 | 1.7 | 1.1 |
| (20)(R3L + R3R)/(R3L − R3R) | −0.34 | −0.12 | 0.03 | −0.16 |
| (21)Σd/Dmaxair | 4.82 | 4.95 | 4.66 | 4.29 |
| (22)D1Ls/FL | 2.67 | 2.59 | 2.30 | 2.61 |

|  | Example 9 | Example 10 | Example 11 | Example 12 |
|---|---|---|---|---|
| (1)αmax − αmin | 5.6E−06 | 5.6E−06 | 5.6E−06 | 5.6E−06 |
| (2)R1R/FL | 1.35 | 1.34 | 1.57 | 1.47 |
| (3)D1Ls/DsF | 1.86 | 1.93 | 2.12 | 2.05 |
| (4)FL/R1L | 0.01 | 0.01 | 0.10 | 0.10 |
| (5)R2R/FL | 3.63 | −16.15 | 1.82 | 2.90 |
| (6)FL/R2L | −0.28 | −0.49 | −0.15 | −0.24 |
| (7)Φ1L/IH | 1.60 | 1.59 | 1.86 | 1.75 |
| (8)D1R2L/Σd | 0.24 | 0.25 | 0.23 | 0.24 |
| (9)D2R3L/Σd | 0.05 | 0.05 | 0.10 | 0.07 |
| (10)D3R4L/Σd | 0.14 | 0.13 | 0.14 | 0.15 |
| (11)f1/FL | −2.57 | −2.55 | −3.55 | −3.32 |
| (12)f2/FL | −3.31 | −4.41 | −2.65 | −3.19 |
| (13)f3/FL | 1.25 | 1.36 | 1.13 | 1.16 |
| (14)Σd/FL | 4.12 | 4.19 | 4.33 | 4.05 |
| (15)vd1/vd3 | 1.9 | 1.9 | 1.9 | 1.9 |
| (16)vd2/vd3 | 1.9 | 1.9 | 1.9 | 1.9 |
| (17)vd3/vd4 | 0.5 | 0.5 | 0.5 | 0.5 |
| (18)f1/R1L | −0.022 | −0.022 | −0.345 | −0.342 |
| (19)f2/R2L | 0.9 | 2.2 | 0.4 | 0.8 |
| (20)(R3L + R3R)/(R3L − R3R) | −0.16 | −0.33 | 0.07 | 0.15 |
| (21)Σd/Dmaxair | 4.18 | 3.97 | 4.33 | 4.13 |
| (22)D1Ls/FL | 2.64 | 2.72 | 2.90 | 2.68 |

|  | Example 13 | Example 14 | Example 15 | Example 16 |
|---|---|---|---|---|
| (1)αmax − αmin | 5.6E−06 | 5.6E−06 | 5.6E−06 | 5.6E−06 |
| (2)R1R/FL | 1.74 | 1.29 | 1.91 | 1.30 |
| (3)D1Ls/DsF | 2.29 | 1.68 | 1.78 | 1.71 |
| (4)FL/R1L | 0.08 | 0.12 | 0.14 | 0.11 |
| (5)R2R/FL | 1.05 | 0.77 | 0.84 | 0.84 |
| (6)FL/R2L | −0.12 | −0.14 | −0.08 | −0.17 |
| (7)Φ1L/IH | 1.97 | 1.55 | 1.63 | 1.71 |
| (8)D1R2L/Σd | 0.23 | 0.23 | 0.14 | 0.21 |
| (9)D2R3L/Σd | 0.07 | 0.04 | 0.12 | 0.06 |
| (10)D3R4L/Σd | 0.18 | 0.21 | 0.24 | 0.17 |
| (11)f1/FL | −3.83 | −2.95 | −4.97 | −2.90 |
| (12)f2/FL | −1.74 | −1.28 | −1.47 | −1.35 |
| (13)f3/FL | 1.27 | 0.89 | 1.23 | 0.97 |
| (14)Σd/FL | 4.77 | 3.73 | 4.32 | 4.29 |
| (15)vd1/vd3 | 1.9 | 1.9 | 1.9 | 1.9 |
| (16)vd2/vd3 | 1.9 | 1.9 | 1.9 | 1.9 |
| (17)vd3/vd4 | 0.5 | 0.5 | 0.5 | 0.5 |
| (18)f1/R1L | −0.292 | −0.360 | −0.672 | −0.313 |
| (19)f2/R2L | 0.2 | 0.2 | 0.1 | 0.2 |
| (20)(R3L + R3R)/(R3L − R3R) | 0.05 | −0.15 | −0.03 | −0.34 |
| (21)Σd/Dmaxair | 4.42 | 4.44 | 4.24 | 4.82 |
| (22)D1Ls/FL | 3.07 | 2.30 | 2.72 | 2.70 |
| (23)|Fc/FL| |  |  |  | 61.85 |

Figure 17:
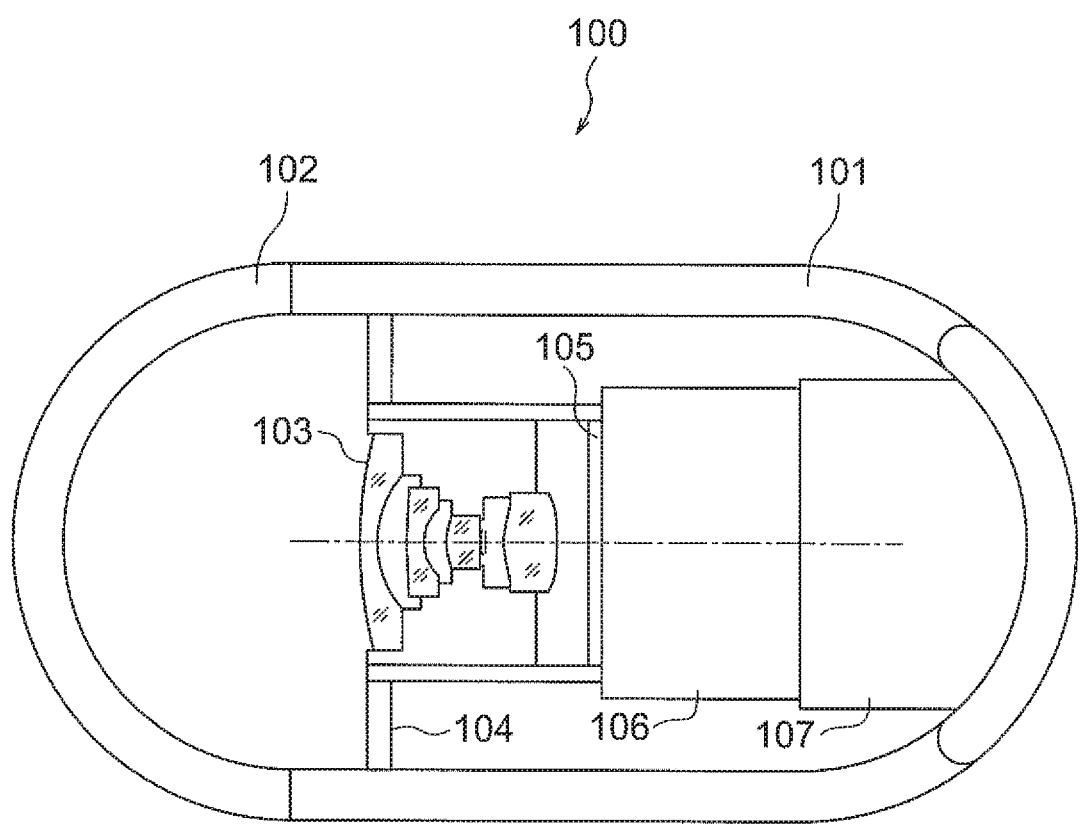
FIG. 17 is a diagram showing a schematic arrangement of a capsule endoscope.

FIG. 17 illustrates an example of an image pickup apparatus. In this example, the image pickup apparatus is a capsule endoscope. A capsule endoscope 100 includes a capsule cover 101 and a transparent cover 102. An outer covering of the capsule endoscope 100 is formed by the capsule cover 101 and the transparent cover 102.

The capsule cover 101 includes a central portion having a substantially circular cylindrical shape, and a bottom portion having a substantially bowl shape. The transparent cover 102 is disposed at a position facing the bottom portion, across the central portion. The transparent cover 102 is formed by a transparent member having a substantially bowl shape. The capsule cover 101 and the transparent cover 102 are connected consecutively to be mutually watertight.

An interior of the capsule endoscope 100 includes an image forming optical system 103, an illumination unit 104, an image sensor 105, a drive control unit 106, and a signal processing unit 107. Although it is not shown in the diagram, the interior of the capsule endoscope 100 is provided with an electric-power receiving unit and a transmitting unit.

Illumination light is irradiated from the illumination unit 104. The illumination light passes through the transparent cover 102 and is irradiated to an object. Light from the object is incident on the image forming optical system 103. An optical image of the object is formed at an image position by the image forming optical system 103.

The optical image is picked up by the image sensor 105. A drive and control of the image sensor 105 is carried out by the drive control unit 106. Moreover, an output signal from the image sensor 105 is processed by the signal processing unit 107 according to the requirement.

Here, for the image forming optical system 103, the optical system according to the abovementioned example 1 for instance, is used. In such manner, the image forming optical system 103 has a wide angle of view and an appropriate back focus, and in which an off-axis aberration is corrected favorably and a fluctuation in the focal length with respect to the temperature change is small, while being small-sized. Consequently, in the image forming optical system 103, a wide-angle optical image having a high resolution is acquired.

Moreover, the capsule endoscope 100 includes an optical system having a wide angle of view and an appropriate back focus, and in which an off-axis aberration is corrected favorably and a fluctuation in the focal length with respect to the temperature change is small, while being small-sized. Consequently, in the capsule endoscope 100, it is possible to acquire a wide-angle image with high resolution, while being small-sized.

Figure 18A:
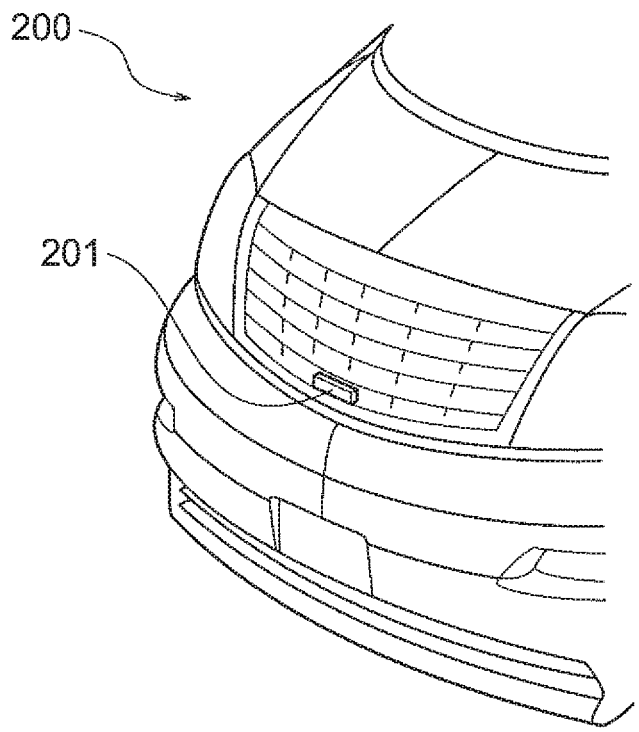
FIG. 18A and FIG. 18B are diagrams showing a car-mounted camera.
Figure 18B:
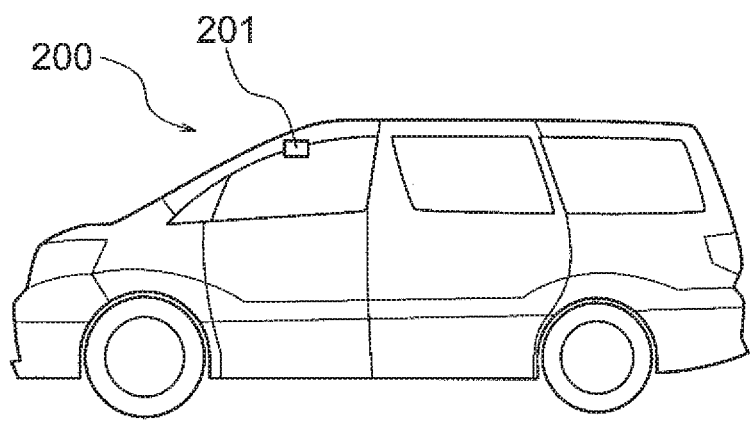

FIG. 18A and FIG. 18B are diagrams illustrating another example of an image pickup apparatus. In this example, the image pickup apparatus is a car-mounted camera. FIG. 18A is a diagram illustrating an example of a car-mounted camera mounted at an outside of a car, and FIG. 18B is a diagram illustrating an example of a car-mounted camera mounted inside a car.

As shown in FIG. 18A, a car-mounted camera 201 is provided to a front grill of an automobile 200. The car-mounted camera 201 includes an image forming optical system and an image sensor.

For the image forming optical system of the car-mounted camera 201, the optical system according to the abovementioned example 1 is used. Consequently, an optical image of an extremely wide range (the angle of view of about 160°) is formed.

As shown in FIG. 18B, the car-mounted camera 201 is provided near a ceiling of the automobile 200. An action and an effect of the car-mounted camera 201 are as have already been described. In the car-mounted camera 201, while being small-sized, it is possible to acquire a wide-angle image with high resolution.

According to the image pickup apparatus of the present embodiment, it is possible to provide an image pickup apparatus equipped with an optical system which, while being small-sized, has a wide angle of view and an appropriate back focus, and in which an off-axis aberration is corrected favorably and a fluctuation in the focal length with respect to the temperature change is small. Moreover, it is possible to provide an optical apparatus which, while being small-sized, is capable of achieving a high-resolution wide-angle optical image.

As described above, the image pickup apparatus according to the present invention is suitable for an image pickup apparatus equipped with an optical system which, while being small-sized, has a wide angle of view and an appropriate back focus, and in which an off-axis aberration is corrected favorably and a fluctuation in the focal length with respect to the temperature change is small. Moreover, the optical apparatus according to the present invention is suitable for an optical apparatus which, while being small-sized, is capable of achieving a high-resolution wide-angle image.

What is claimed is:

1. An image pickup apparatus, comprising:
an optical system which includes a plurality of lenses and an aperture stop; and
an image sensor which is disposed at an image position of the optical system, wherein
the optical system includes in order from an object side,
a first lens having a negative refractive power,
a second lens having a negative refractive power,
a third lens having a positive refractive power,
a fourth lens, and
an optical member through which light passes, on the object side of the optical system,
both surfaces of the optical member is curved surfaces, and
the following conditional expressions (1), (3), and (23) are satisfied:

$$\alpha max - \alpha min < 4.0 \times 10^{-5}/°C. \quad (1),$$

$$0.2 < D1Ls/DsF < 3.0 \quad (3), \text{ and}$$

$$30 < |Fc/FL| \quad (23)$$

where,
α max denotes a largest coefficient of linear expansion among coefficients of linear expansion at 20 degrees, of the plurality of lenses,
α min denotes a smallest coefficient of linear expansion among the coefficients of linear expansion at 20 degrees, of the plurality of lenses,
D1Ls denotes a distance on an optical axis from an object-side surface of the first lens up to an object-side surface of the aperture stop,
DsF denotes a distance on the optical axis from an image-side surface of the aperture stop up to a lens surface positioned nearest to image.
Fc denotes a focal length of the optical member, and
FL denotes a focal length of the overall optical system.

2. The image pickup apparatus according to claim 1, wherein the following conditional expression (2) is satisfied:

$$0.1 < R1R/FL < 2.5 \quad (2),$$

where,
R1R denotes a paraxial radius of curvature of an image-side surface of the first lens,
FL denotes the focal length of the overall optical system.

3. The image pickup apparatus according to claim 1, wherein the following conditional expression (4) is satisfied:

$$-0.01 < FL/R1L < 1.0 \quad (4),$$

where,
R1L denotes a paraxial radius of curvature of an object-side surface of the first lens, and
FL denotes the focal length of the overall optical system.

4. The image pickup apparatus according to claim 1, wherein the following conditional expression (5) is satisfied:

$$0.1 < R2R/FL < 50 \quad (5),$$

where,
R2R denotes a paraxial radius of curvature of an image-side surface of the second lens, and
FL denotes the focal length of the overall optical system.

5. The image pickup apparatus according to claim 1, wherein the following conditional expression (6) is satisfied:

$$-1.0 < FL/R2L < 0.8 \quad (6),$$

where,
R2L denotes a paraxial radius of curvature of an object-side surface of the second lens, and
FL denotes the focal length of the overall optical system.

6. The image pickup apparatus according to claim 1, wherein the following conditional expression (7):

$$0.5 < \Phi 1L/IH < 3.0 \quad (7),$$

where,
IH denotes a maximum image height, and
Φ1L denotes an effective aperture at the object-side surface of the first lens.

7. An image pickup apparatus according to claim 1, wherein
the optical system includes a lens surface positioned nearest to object and a lens surface positioned nearest to image, and
the following conditional expression (8) is satisfied:

$$0.05 < D1R2L/\Sigma d < 0.5 \quad (8),$$

where,
D1R2L denotes an air space from the image-side surface of the first lens up to the object-side surface of the second lens, and
Σd denotes a distance from the lens surface positioned nearest to object up to the lens surface positioned nearest to image.

8. The image pickup apparatus according to claim 1, wherein
the optical system includes a lens surface positioned nearest to object and a lens surface positioned nearest to image, and
the following conditional expression (9) is satisfied:

$$0.01 < D2R3L/\Sigma d < 0.3 \quad (9),$$

where,
D2R3L denotes an air space from the image-side surface of the second lens up to an object-side surface of the third lens, and
Σd denotes a distance from the lens surface positioned nearest to object up to the lens surface positioned nearest to image.

9. The image pickup apparatus according to claim 1, wherein
the optical system includes a lens surface positioned nearest to object and a lens surface positioned nearest to image, and the following conditional expression (10) is satisfied:

$$0.05 < D3R4L/\Sigma d < 0.5 \quad (10),$$

where,
D3R4L denotes an air space from an image-side surface of the third lens up to an object-side surface of the fourth lens, and
Σd denotes a distance from the lens surface positioned nearest to object up to the lens surface positioned nearest to image.

10. The image pickup apparatus according to claim 1, wherein the following conditional expression (11) is satisfied:

$$-10.0 < f1/FL < -0.5 \quad (11),$$

where,
f1 denotes a focal length of the first lens, and
FL denotes the focal length of the overall optical system.

11. The image pickup apparatus according to claim 1, wherein the following conditional expression (12) is satisfied:

$$-10.0 < f2/FL < -0.1 \quad (12),$$

where,
f2 denotes a focal length of the second lens, and
FL denotes the focal length of the overall optical system.

12. The image pickup apparatus according to claim 1, wherein the following conditional expression (13) is satisfied:

$$0.5 < f3/FL < 20.0 \quad (13),$$

where,
f3 denotes a focal length of the third lens, and
FL denotes the focal length of the overall optical system.

13. The image pickup apparatus according to claim 1, wherein
the optical system includes a lens surface positioned nearest to object and a lens surface positioned nearest to image,
the following conditional expression (14) is satisfied:

$$2.0 < \Sigma d/FL < 8.0 \quad (14),$$

where,
Σd denotes a distance from the lens surface positioned nearest to object up to the lens surface positioned nearest to image, and
FL denotes a focal length of the overall optical system.

14. The image pickup apparatus according to claim 1, wherein the following conditional expression (15) is satisfied:

$$0.8 < vd1/vd3 < 3.5 \quad (15),$$

where,
vd1 denotes Abbe number for the first lens, and
vd3 denotes Abbe number for the third lens.

15. The image pickup apparatus according to claim 1, wherein the following conditional expression (16) is satisfied:

$$0.8 < vd2/vd3 < 3.5 \quad (16),$$

where,
vd2 denotes Abbe number for the second lens, and
vd3 denotes Abbe number for the third lens.

16. The image pickup apparatus according to claim 1, wherein the following conditional expression (17) is satisfied:

$$0.3 < vd3/vd4 < 0.8 \quad (17),$$

where,
vd3 denotes Abbe number for the third lens, and
vd4 denotes Abbe number for the fourth lens.

17. The image pickup apparatus according to claim 1, wherein the following conditional expression (18) is satisfied:

$$-1.0 < f1/R1L < 0 \quad (18),$$

where,
f1 denotes a focal length of the first lens, and
R1L denotes a paraxial radius of curvature of the object-side surface of the first lens.

18. The image pickup apparatus according to claim 1, wherein the following conditional expression (19) is satisfied:

$$-1.0 < f2/R2L < 3.0 \quad (19),$$

where,
f2 denotes a focal length of the second lens, and
R2L denotes a paraxial radius of curvature of the object-side surface of the second lens.

19. The image pickup apparatus according to claim 1, wherein the following conditional expression (20) is satisfied:

$$-1.0 < (R3L+R3R)/(R3L-R3R) < 0.5 \quad (20),$$

where,
R3L denotes a paraxial radius of curvature of the object-side surface of the third lens, and
R3R denotes a paraxial radius of curvature of the image-side surface of the third lens.

20. The image pickup apparatus according to claim 1, wherein
the optical system includes a lens surface positioned nearest to object and a lens surface positioned nearest to image, and
the following conditional expression (21) is satisfied:

$$2.0 < \Sigma d/Dmaxair < 9.0 \quad (21),$$

where,
Σd denotes a distance from the lens surface positioned nearest to object up to the lens surface positioned nearest to image, and
Dmaxair denotes a largest air space among air spaces between the lens surface positioned nearest to object and the lens surface positioned nearest to image.

21. An image pickup apparatus according to claim 1, wherein
the optical system includes an apertures stop, and
the following conditional expression (22) is satisfied:

$$1.0 < D1Ls/FL < 5.0 \quad (22),$$

where,
D1Ls denotes the distance on the optical axis from the object-side surface of the first lens up to an object-side surface of the apertures stop, and
FL denotes the focal length of the overall optical system.

22. The image pickup apparatus according to claim 1, wherein a half angle of view is not less than 65 degrees.

23. An optical apparatus, comprising:
an image pickup apparatus according to claim 1; and
a signal processing circuit.

* * * * *